US009410956B1

(12) United States Patent
Cheng

(10) Patent No.: US 9,410,956 B1
(45) Date of Patent: Aug. 9, 2016

(54) MICRO-RNA PROFILING IN OVARIAN CANCER

(75) Inventor: Jin Q. Cheng, Tampa, FL (US)

(73) Assignee: University of South Florida, Tampa, FL (US)

( * ) Notice: Subject to any disclaimer, the term of this patent is extended or adjusted under 35 U.S.C. 154(b) by 305 days.

(21) Appl. No.: 12/534,618

(22) Filed: Aug. 3, 2009

Related U.S. Application Data

(60) Provisional application No. 61/085,639, filed on Aug. 1, 2008.

(51) Int. Cl.
*G01N 33/574* (2006.01)
(52) U.S. Cl.
CPC .... *G01N 33/57449* (2013.01); *C12Q 2600/178* (2013.01)
(58) Field of Classification Search
None
See application file for complete search history.

(56) References Cited

U.S. PATENT DOCUMENTS 8,216,784 B2 * 7/2012 Taylor et al. ............ 435/6.1
2009/0192127 A1 * 7/2009 Scheuring et al. ........ 514/171

OTHER PUBLICATIONS

Chan, et al. (2002) Inhibition of Growth and Sensitization to Cisplatin-Mediated Killing of Ovarian Cancer Cells by Polyphenolic Chemopreventive Agents. Journal of Cellular Physiology, v.194:63-70.*
Zhang, et al. (2007) Micrornas Exhibit High Frequency Genomic Alterations in Human Cancer. PNAS, v.103(24): Supplemental Table 8 Only. The main document was provided by Applicant on an IDS on Oct. 26, 2009.*
Nam, et al. (2008) Microrna Expression Profiles in Serous Ovarian Carcinoma, Clinical Cancer Research, v.14(9):2690-5.*
Volinia, et al. (2006) A Microrna Expression Signature of Human Solid Tumors Defines Cancer Gene Targets, Proceedings of the National Academy of Sciences, v.103(7):2257-61.*
Yang, et al. (2008) Microrna Expression Profiling in Human Ovarian Cancer: MIR-214 Induces Cell Survival and Cisplatin Resistance by Targeting PTEN, Cancer Research, v.68(2):425-33.*
Valoczi, et al. (2004) Sensitive and specific detection of microRNAs by northern blot analysis using LNA-modified oligonucleotide probes. Nucleic Acids Research, V.32(22):e175[1]-e175[7].*
Blenkiron, et al., MiRNAs in Cancer: Approaches, Aetiology, Diagnostics and Therapy, Human Molecular Genetics, 2007, vol. 16, Review Issue 1, pp. R106-R113.
Zhang, et al., MicroRNAs as Oncogenes and Tumor Suppressors, Developmental Biology, 2007, vol. 302, pp. 1-12.
Iorio, et al., MicroRNA Signatures in Human Ovarian Cancer, Cancer Research, 2007, vol. 67, No. 18, pp. 8699-8707.
Wu, et al., Effect of Tumor Suppressor Gene PTEN on the Resistance to Cisplatin in Human Ovarian Cancer Cell Lines and Related Mechanisms, Cancer Letters, 2008, vol. 271, pp. 260-271.
Cannistra, Cancer of the Ovary, The New England Journal of Medicine, 2004, vol. 351, No. 24, pp. 2519-2529.
Feeley, et al., Precursor Lesions of Ovarian Epithelial Malignancy, Histopathology, 2001, vol. 38, pp. 87-95.
Bell, Origins and Molecular Pathology of Ovarian Cancer, Modern Pathology, 2005, vol. 18, pp. S19-S32.
Lagos-Quintana, et al., Identification of Novel Genes Coding for Small Expressed RNAs, Science, 2001, vol. 294, pp. 853-858.
Bartel, MicroRNAs: Genomics, Biogenesis, Mechanism, and Function, Cell, 2004, vol. 116, pp. 281-297.
Calin, et al., Frequent Deletions and Down-Regulation of Micro-RNA Genes MiR15 and MiR16 at 13q14 in Chronic Lymphocytic Leukemia, PNAS, 2002, vol. 99, No. 24, pp. 15524-15529.
Zhang, et al., MicroRNAs Exhibit High Frequency Genomic Alterations in Human Cancer, PNAS, 2006, vol. 103, No. 24, pp. 9136-9141.
Lu, et al., MicroRNA Expression Profiles Classify Human Cancers, Nature, 2005, vol. 435, pp. 834-838.
Chan, et al., MicroRNA-21 is an Antiapoptotic Factor in Human Glioblastoma Cells, Cancer Research, 2005, vol. 65, No. 14, pp. 6029-6033.
Takamizawa, et al., Reduced Expression of the let-7 MicroRNAs in Human Lung Cancers in Association with Shortened Postoperative Survival, Cancer Research, 2004, vol. 64, pp. 3753-3756.
He, et al., The Role of MicroRNA Genes in Papillary Thyroid Carcinoma, PNAS, 2005, vol. 102, No. 52, pp. 19075-19080.
Iorio, et al., MicroRNA Gene Expression Deregulation in Human Breast Cancer, Cancer Research, 2005, vol. 65, No. 16, pp. 7065-7070.
Volinia, et al., A MicroRNA Expression Signature of Human Solid Tumors Defines Cancer Gene Targets, PNAS, 2006, vol. 103, No. 7, pp. 2257-2261.
Lee, et al., Expression Profiling Identifies MicroRNA Signature in Pancreatic Cancer, Int. J. Cancer, 2006, vol. 120, pp. 1046-1054.
Gaur, et al. Characterization of MicroRNA Expression Levels and Their Biological Correlates in Human Cancer Cell Lines, Cancer Research, 2007, vol. 67, No. 6, pp. 2456-2468.

(Continued)

*Primary Examiner* — Jennifer McDonald
(74) *Attorney, Agent, or Firm* — Michele L. Lawson; Smith & Hopen, P.A.

(57) ABSTRACT

MicroRNAs (miRNAs) represent a novel class of genes that function as negative regulators of gene expression and have recently been implicated in several cancers. However, aberrant miRNA expression and its clinicopathological significance in human ovarian cancer have not been well documented. Numerous miRNAs are shown altered in human ovarian cancer, significantly miR-214, -199a*, -200a, -100, -125b, -30d, -221, -222, -126, and -24. Four miRNAs (miR-221, miR-222, miR-126, and miR-24) were found to be deregulated in all four histological types of ovarian carcinoma (serous, mucinous, endometrioid, and clear cell). Frequent deregulation of miR-214, -199a*, -200a and -100 was demonstrated in ovarian cancers. Significantly, miR-214 induces cell survival and cisplatin resistance through targeting down-regulation of proteins activating the Akt pathway. Inhibition of Akt using Akt inhibitor, API-2/triciribine, or PTEN cDNA lacking 3'UTR largely abrogates miR-214 induced cell survival. These findings indicate that deregulation of miRNAs is a recurrent event in human ovarian cancer and that miR-214 induces cell survival and cisplatin resistance primarily through targeting the PTEN/Akt pathway.

1 Claim, 28 Drawing Sheets

(56) References Cited

OTHER PUBLICATIONS

Johnson, et al., Ras is Regulated by the let-7 MicroRNA Family, Cell, 2005, vol. 120, pp. 635-647.

Metzler, et al., High Expression of Precursor MicroRNA-155/BIC RNA in Children with Burkitt Lymphoma, Genes, Chromosomes & Cancer, 2004, vol. 39, pp. 167-169.

Eis, et al., Accumulation of Mir-155 and BIC RNA in Human B Cell Lymphomas, PNAS, 2005, vol. 102, No. 10, pp. 3627-3632.

Yang, et al., Aurora-A Kinase Regulates Telomerase Activity Through C-Myc in Human Ovarian and Breast Epithelial Cells, Cancer Research, 2004, vol. 64, pp. 463-467.

Yang, et al., Akt/Protein Kinase B Signaling Inhibitor-2, a Selective Small Molecule Inhibitor of Akt Signaling with Antitumor Activity in Cancer Cells Overexpressing Akt, Cancer Research, 2004, vol. 64, pp. 4394-4399.

Yuan, et al., AKT2 Inhibition of Cisplatin-Induced JNK/p38 and Bax Activation by Phosphorylation of ASK1, The Journal of Biological Chemistry, 2003, vol. 278, No. 26, pp. 23432-23440.

Flynt, et al., Zebrafish MiR-214 Modulates Hedgehog Signaling to Specify Muscle Cell Fate, Nature Genetics, 2007, vol. 39, No. 2, pp. 259-263.

Testa, et al., AKT Plays a Central Role in Tumorigenesis, PNAS, 2001, vol. 98, No. 20, pp. 10983-10985.

Yan, et al., Over-Expression of PTEN Sensitizes Human Ovarian Cancer Cells to Cisplatin-Induced Apoptosis in a P53-Dependent Manner, Gynecologic Oncology, 2006, vol. 102, pp. 348-355.

Negrini, et al., MicroRNAs in Human Cancer: From Research to Therapy, Journal of Cell Science, 2007, vol. 120, No. 11, pp. 1833-1840.

Kutay, et al., Downregulation of MiR-122 in the Rodent and Human Hepatocellular Carcinomas, Journal of Cellular Biochemistry, 2006, vol. 99, pp. 671-678.

Cummins, et al., Implications of Micro-RNA Profiling for Cancer Diagnosis, Oncogene, 2006, vol. 25, pp. 6220-6227.

Dalmay, et al., MicroRNAs and the Hallmarks of Cancer, Oncogene, 2006, vol. 25, pp. 6170-6175.

Tricoli, et al., MicroRNA: Potential for Cancer Detection, Diagnosis, and Prognosis, Cancer Research, 2007, vol. 67, No. 10, pp. 4553-4555.

Roldo, et al., MicroRNA Expression Abnormalities in Pancreatic Endocrine and Acinar Tumors are Associated with Distinctive Pathologic Features and Clinical Behavior, Journal of Clinical Oncology, 2006, vol. 24, No. 29, pp. 4677-4684.

Obata, et al., Frequent PTEN/MMAC Mutations in Endometrioid but not Serous or Mucinous Epithelial Ovarian Tumors, Cancer Research, 1998, vol. 58, pp. 2095-2097.

Schondorf, et al., Hypermethylation of the PTEN Gene in Ovarian Cancer Cell Lines, Cancer Letters, 2004, vol. 207, pp. 215-220.

Trimble, et al., Long-Term Survival and Patterns of Care in Women with Ovarian Tumors of Low Malignant Potential, Gynecologic Oncology, 2002, vol. 86, pp. 34-37.

Rao, Fertility-Sparing Surgery for Ovarian Low Malignant Potential Tumors, Gynecologic Oncology, 2005, vol. 98, pp. 263-266.

Disaia, et al., The Adnexal Mass and Early Ovarian Cancer, Clinical Gynecologic Oncology, 2002, pp. 259-287.

Aghajanian, Clinical Update: Novel Targets in Gynecologic Malignancies, Seminars in Oncology, 2004, vol. 31, pp. 22-26.

Hua Yang, William Kong, Lili He, et al., MicroRNA Expression Profiling in Human Ovarian Cancer: miR-214 Induces Cell Survival and Cisplatin Resistance by Targeting PTEN, Cancer Research, vol. 68, Issue 2, Jan. 15, 2008.

\* cited by examiner

Figure 19

SEQUENCE LISTING

```
<160> NUMBER OF SEQ ID NOS: 19

<210> SEQ ID NO 1
<211> LENGTH: 21
<212> TYPE: RNA
<213> ORGANISM: artificial sequence
<220> FEATURE:
<223> OTHER INFORMATION: seed sequence for miR-214

<400> SEQUENCE: 1
cugccugucu gugccugcug u                                             21

<210> SEQ ID NO 2
<211> LENGTH: 22
<212> TYPE: RNA
<213> ORGANISM: artificial sequence
<220> FEATURE:
<223> OTHER INFORMATION: seed sequence for miR-214 compared to p53

<400> SEQUENCE: 2
ugacggacag acacggacga ca                                            22
```

```
<210> SEQ ID NO 3
<211> LENGTH: 22
<212> TYPE: RNA
<213> ORGANISM: artificial sequence
<220> FEATURE:
<223> OTHER INFORMATION: knockdown seed sequence for miR-100

<400> SEQUENCE: 3
aacccguaga uccgaacuug ug                                            22

<210> SEQ ID NO 4
<211> LENGTH: 66
<212> TYPE: DNA
<213> ORGANISM: artificial sequence
<220> FEATURE:
<223> OTHER INFORMATION: Leading strand of psuper-mir-100 vector

<400> SEQUENCE: 4
gatcccccac aagttcggat ctacgggttt tcaagagaaa cccgaagatc cgaacttgtg   60
tttttta                                                             66

<210> SEQ ID NO 5
<211> LENGTH: 63
<212> TYPE: DNA
<213> ORGANISM: artificial sequence
<220> FEATURE:
<223> OTHER INFORMATION: Lagging strand of psuper-mir-100 vector

<400> SEQUENCE: 5
agcttaaaaa cacaagttcg gatctacggg tttctcttga aacccgtag atccgaactt    60 gtg                                                                 63

<210> SEQ ID NO 6
<211> LENGTH: 35
<212> TYPE: DNA
<213> ORGANISM: Homo Sapiens

<400> SEQUENCE: 6
ttattttact agttttcaat cataatacct gctgt                              35

<210> SEQ ID NO 7
<211> LENGTH: 35
<212> TYPE: DNA
<213> ORGANISM: Mus Musculus

<400> SEQUENCE: 7
ttatttttat taattttcaa tcatatacct actgt                              35

<210> SEQ ID NO 8
<211> LENGTH: 35
<212> TYPE: DNA
<213> ORGANISM: Rattus Norvegicus

<400> SEQUENCE: 8
ttatttttat taattttcaa tcatatacct actgt                              35

<210> SEQ ID NO 9
<211> LENGTH: 21
<212> TYPE: DNA
<213> ORGANISM: artificial sequence
<220> FEATURE:
<223> OTHER INFORMATION: mutations of the 3'UTR of PTEN for creating the
      mutant luciferase reporter construct

<400> SEQUENCE: 9
```
ttcaatcata atacctgaca t                     21

<210> SEQ ID NO 10
<211> LENGTH: 22
<212> TYPE: DNA
<213> ORGANISM: artificial sequence
<220> FEATURE:
<223> OTHER INFORMATION: 3' UTR of p53

<400> SEQUENCE: 10
gggagttgtc aagtcttgct gg                    22

<210> SEQ ID NO 11
<211> LENGTH: 22
<212> TYPE: DNA
<213> ORGANISM: artificial sequence
<220> FEATURE:
<223> OTHER INFORMATION: probe sequence for miR-199a

<400> SEQUENCE: 11
aaccaatgtg cagactactg ta                    22

<210> SEQ ID NO 12
<211> LENGTH: 21
<212> TYPE: DNA
<213> ORGANISM: artificial sequence
<220> FEATURE:
<223> OTHER INFORMATION: probe sequence for miR-214

<400> SEQUENCE: 12
ctgcctgtct gtgcctgctg t                     21

<210> SEQ ID NO 13
<211> LENGTH: 22
<212> TYPE: DNA
<213> ORGANISM: artificial sequence
<220> FEATURE:
<223> OTHER INFORMATION: probe sequence for miR-1005

<400> SEQUENCE: 13
cacaagttcg gatctacggg tt                    22

<210> SEQ ID NO 14
<211> LENGTH: 22
<212> TYPE: DNA
<213> ORGANISM: artificial sequence
<220> FEATURE:
<223> OTHER INFORMATION: probe sequence for miR-200a

<400> SEQUENCE: 14
acatcgttac cagacagtgt ta                    22

<210> SEQ ID NO 15
<211> LENGTH: 23
<212> TYPE: RNA
<213> ORGANISM: artificial sequence
<220> FEATURE:
<223> OTHER INFORMATION: 2'-O-me-scrambled miR

<400> SEQUENCE: 15
aaaaccuuuu gaccgagcgu guu                   23

<210> SEQ ID NO 16
<211> LENGTH: 28
<212> TYPE: DNA

```
<213> ORGANISM: artificial sequence
<220> FEATURE:
<223> OTHER INFORMATION: miR-214 sense primer for expression plasmid

<400> SEQUENCE: 16
cacctttctc cctttcccct tactctcc                                          28

<210> SEQ ID NO 17
<211> LENGTH: 24
<212> TYPE: DNA
<213> ORGANISM: artificial sequence
<220> FEATURE:
<223> OTHER INFORMATION: miR-214 antisense primer for expression plasmid

<400> SEQUENCE: 17
tttcataggc accactcact ttac                                              24

<210> SEQ ID NO 18
<211> LENGTH: 28
<212> TYPE: DNA
<213> ORGANISM: artificial sequence
<220> FEATURE:
<223> OTHER INFORMATION: miR-199a sense primer for expression plasmid

<400> SEQUENCE: 18
caccgcccag aagccacgat cccaaacc                                          28

<210> SEQ ID NO 19
<211> LENGTH: 22
<212> TYPE: DNA
<213> ORGANISM: artificial sequence
<220> FEATURE:
<223> OTHER INFORMATION: miR-199a antisense primer for expression
      plasmid

<400> SEQUENCE: 19
tgcctttccc cagtgcctct tc                                                22
```

MICRO-RNA PROFILING IN OVARIAN CANCER

CROSS REFERENCE TO RELATED APPLICATIONS

This application claims priority under 35 U.S.C. §119(e) to U.S. provisional patent application No. 61/085,639 filed Aug. 1, 2008 which is hereby incorporated by reference into this disclosure.

GOVERNMENT SUPPORT

This invention was made with government support under Grant Nos. CA77935; CA107078 and DAMD17-02-1-0671 awarded by the National Institutes of Health and Department of Defense. The Government has certain rights in the invention.

FIELD OF INVENTION

This invention relates to genetic cancer regulators. Specifically, the invention is a method of detecting cancer and treatment methods based on a series of micro-RNA molecules.

BACKGROUND OF THE INVENTION

Epithelial ovarian cancer is the most common gynecologic malignancy and the sixth most common cancer in women, causing 125,000 deaths yearly. (Cannistra S. A., Cancer of the ovary, N Engl J Med, 2004; 351:2519-29) The survival rate at five years after initial diagnosis is only 30% due to the late stage diagnosis for greater than 70% of ovarian cancers. When ovarian cancer is diagnosed in its early stages (e.g. still organ confined), the survival rate at five years exceeds 90%. However, only 19% of all ovarian cancers are diagnosed at the early stage. (Feely K. M. et. al., Precursor lesions of ovarian epithelial malignancy, Histopathology, 2001; 38:87-95) Ovarian cancers occur as four major subtypes: serous, mucinous, endometrioid, and clear cell. Each of these histologic types is associated with distinct molecular and morphologic genetic alterations. (Bell D. A., Origins and molecular pathology of ovarian cancer, Mod Pathol, 2005; 18 Suppl 2:S19-32)

MicroRNAs (miRNAs) are a class of 22-nt noncoding RNAs, which are evolutionarily conserved and function as negative regulators of gene expression. Like conventional protein-coding mRNA, miRNAs are transcribed by RNA polymerase II, spliced and polyadenylated (called primitive miRNA or pri-miRNA). However, unlike mRNA, the pri-miRNAs contain a stem-loop structure that can be recognized and excised by the RNAi machinery to generate hairpin 'precursor' miRNAs (pre-miRNA) that are, ~70 nt in animals or ~100 nt in plants. Pre-miRNAs are cleaved by the cytoplasmic RNase III Dicer into a ~22-nucleotide miRNA duplex: one strand (miRNA*) of the short-lived duplex is degraded, whereas the other strand serves as a mature miRNA. The mature miRNA then guides a complex called miRNP (miRNA-containing ribonucleo-protein particles) to the complementary site(s) in the 3' untranslated region (UTR) of a target mRNA. Consequently, translation blockade or mRNA degradation will occur depending on whether it is partially matched or completely matched with the target genes, respectively (Lagos-Quintana, et al., Identification of novel genes coding for small expressed RNAs. Science 2001; 294:853-8). Moreover, the levels of individual miRNAs are dramatically changed in different cell types and different developmental stages, suggesting that miRNA plays a role in cell growth, differentiation, and programmed cell death (Lagos-Quintana, et al., 2001; Bartel, D., MicroRNAs: genomics, biogenesis, mechanism, and function. Cell 2004; 116: 281-97).

miRNAs have been shown to be aberrantly expressed or mutated in human cancer, indicating that they may function as a novel class of oncogenes or tumor suppressor genes (Calin G A, et al., Frequent deletions and down-regulation of microRNA genes miR15 and miR16 at 13q14 in chronic lymphocytic leukemia. Proc Natl Acad Sci USA 2002, 99:15524-9; Zhang, L., et al., microRNAs exhibit high frequency genomic alterations in human cancer. Proc Natl Acad Sci USA. 2006, 103:9136-41; Lu, J., et al., MicroRNA expression profiles classify human cancers. Nature 2005, 435:834-8; Chan, J., et al., MicroRNA-21 is an antiapoptotic factor in human glioblastoma cells. Cancer Res. 2005; 65:6029-33; Takamizawa, J., et al., Reduced expression of the let-7 microRNAs in human lung cancers in association with shortened postoperative survival. Cancer Res 2004; 64:3753-6; He, H., et al. The role of microRNA genes in papillary thyroid carcinoma. Proc Natl Acad Sci USA 2005; 102:19075-80). The first evidence of involvement of miRNAs in human cancer came from molecular studies characterizing the 13q14 deletion in human chronic lymphocytic leukemia, which revealed two miRNAs, miR-15a and miR-16-1 (Calin G A, et al., 2002). Subsequently, miRNA deregulation was detected in other human malignancies, including breast carcinoma (Iorio, M. et al., MicroRNA gene expression deregulation in human breast cancer. Cancer Res. 2005; 65:7065-70; Zhang, L., et al., 2006), primary glioblastoma (Lu, J., et al., 2005; Chan, J., et al., 2005), lung cancer (Takamizawa, J., et al., 2004), papillary thyroid carcinoma (He, H., et al., 2005), colon carcinoma (Volinia, S., et al., A microRNA expression signature of human solid tumors defines cancer gene targets. Proc Natl Acad Sci USA. 2006, 103:2257-61.) and pancreatic tumors (Lee, E., et al., Expression profiling identifies microRNA signature in pancreatic cancer. Int J Cancer. 2007, 120:1046-54; Gaur, A., et al., Characterization of microRNA expression levels and their biological correlates in human cancer cell lines. Cancer Res. 2007, 67:2456-68). For instance, the miR-17-92 cluster is upregulated in B-cell lymphomas and lung cancer. miR-143 and -145 are down-regulated in colon carcinomas. A decrease in Let-7 is detected in human lung carcinomas and restoration of its expression induces cell growth inhibition in lung cancer cells (Johnson, S., et al., RAS is regulated by the let-7 microRNA family. Cell 2005, 120:635-47). The BIC gene, which contains the miR-155, is up-regulated in some Burkitt's lymphomas and several other types of lymphomas (Metzler, M., et al., High expression of precursor microRNA-155/BIC RNA in children with Burkitt lymphoma. Genes Chromosomes Cancer 2004, 39:167-9; Eis, P., et al., Accumulation of miR-155 and BIC RNA in human B cell lymphomas. Proc Natl Acad Sci USA 2005, 102:3627-32).

A number of miRNAs were observed deregulated in human ovarian cancer. The deregulation of miRNAs refers to the upregulation or down-regulation of the expression of the specific miRNAs. The aberrant expression of miR-214, -199a*, -200a and -100 was detected in nearly half or over half of ovarian cancers, especially in late stage and high grade tumors. Significantly, miR-214 was demonstrated to negatively regulate PTEN by binding to its 3'UTR leading to inhibition of PTEN translation and activation of Akt pathway. As a result, miR-214 induces cell survival and cisplatin resistance, which were overridden by either small molecule Akt inhibitor or expression of PTEN cDNA lacking 3'UTR

SUMMARY OF INVENTION

An illustrative embodiment of the present invention includes a method of identifying and classifying cancerous cells through the use of miRNAs. The regulation expression patterns of specific miRNAs are determined in both tumor cells and normal cells. These regulation expression patterns of the specific miRNAs are then quantified to determine the differential expression of the miRNAs between tumor cells and normal cells. This quantification can be done through the use of a Phosphorimager.

Potential targets of the specific miRNAs are then determined. This determination can be done, for example, by searching the PicTar and miRBase database as well as sequence alignment analysis using GCG.

In a preferred embodiment, the cancerous cells that are being identified and classified are ovarian cancer cells and the miRNA that is being used is one of the following: miR-214, miR-199a*, miR-200a, miR-100, miR-221, miR-222, miR-126, miR-24, and miR-30d.

Another embodiment of the present invention is a method for determining resistance to platinum-based chemotherapeutics through determining the regulation expression patterns of miRNA in both tumor cells and normal cells after which these patterns are quantified and potential targets are determined.

Preferably the miRNAs that are used are the following: miR-214, miR-199a*, miR-200a, miR-100, miR-221, miR-222, miR-126, miR-24, and miR-30d. Even more preferably the miRNA used is miR-214 and the pathway targeted is PTEN/Akt.

Also disclosed herein is a method of diagnosing ovarian cancer in which the regulation expression patterns of miRNA in both tumor cells and normal cells is determined and the differences quantified. Potential gene targets and pathways targeted by the specific miRNAS is then determined.

In a preferred embodiment, the miRNAs that are targeted are the following: miR-214, miR-199a*, miR-200a, miR-100, miR-221, miR-222. miR-126, miR-24, and miR-30d. More preferably, the miRNA is miR-214 whose target is the PTEN/Akt pathway.

BRIEF DESCRIPTION OF THE DRAWINGS

For a fuller understanding of the invention, reference should be made to the following detailed description, taken in connection with the accompanying drawings, in which:

FIG. 1A: An image showing the Northern blot analysis of 20 μg of total RNA from human primary ovarian tumors and normal ovary tissue were separated on a denaturing 15% polyacrilamide gel and transferred to a GeneScreen Plus membrane. The blot was hybridized with indicated probes.

FIG. 1B: An image showing a list of deregulated miRNAs at more than 1-fold in human ovarian cancer vs., normal ovary.

FIG. 2A: An image of the sequence alignment of human miR-214 (SEQ ID NO:1) with 3'UTR of PTEN. The seed sequence of miR-214 (upper) (SEQ ID NO:1) matches 3'UTR of PTEN from Homo sapiens (SEQ ID NO:2), Mus musculus (SEQ ID NO:3), and Rattus norvegicus (SEQ ID NO:4). Bottom panel shows mutations of the 3'UTR of PTEN (SEQ ID NO:5) or creating the mutant luciferase reporter construct.

FIG. 2B: An image showing miR-214 reduces PTEN protein but not mRNA levels. HIOSE-80 cells (left panels) were transfected with pcDNA3.1/V5-His-Topo-miR-214, -miR199a* and vector alone and immunoblotted with indicated antibodies (panels 1-4). The expression of miR-214 and miR-199a* was determined by qRT-PCR (panels 5 and 6). PTEN mRNA level was measured by RT-PCR (panel 8). U6 (panel 7) and GAPDH (bottom panel) were used for controls. Middle and right panels show knockdown of miR-214 inducing PTEN expression. A2780CP cells were transfected with antisense 2'-O-methyl oligonucleotide targeting miR-214 at concentration of 150 pM/well (6 well plate) with Lipofectamine 2000. Anti-miR199a* and scramble 2'-O-methyl oligonucleotide were used as controls. After incubation of 72 h, cells were lysed and immunoblotted with indicated antibodies (middle). Inhibition of miR-214 and miR-199a* expression by 2'-O-methyl oligonucleotide in A2780CP cells was demonstrated by qRT-PCR (right).

FIG. 2C: An image showing miR-214 inhibits wild-type but not mutated PTEN-3'UTR reporter activity. miR-214-positive A2780CP (left) and miR-214-negative HIOSE-80 cells (right) were transiently transfected with indicated plasmids. Following 36 h incubation, cells were subjected to luciferase assay. The data are the means of three independent experiments, and error bars indicate standard deviations.

FIG. 2D: An image showing representative tumor and normal tissue lysates were analyzed by Western blot with indicated antibodies (panels 1 and 2). Expression of miR-214 was analyzed by qRT-PCR. (panel 3). U6 was used as a control (bottom panel).

FIG. 3A: An image showing RNase protection analysis of miR-214 expression in ovarian cancer cell lines and immortalized human ovarian surface epithelial cells (top). 5S was used as control (bottom).

FIG. 3B: An image showing ectopic expression of miR-214. A2780S and OV119 cells, which express low levels of endogenous miR-214, were transfected with pcDNA3.1N5-His-Topo-miR-214 or vector alone. Following G418 selection, cells were subjected to qRT-PCR analysis for expression of miR-214 (top) and U6 (bottom).

FIG. 3C: An image showing the expression of miR-214 renders A2780S and OV119 cells resistant to cisplatin. The vector (Topo)- and miR-214-transfected cells were treated with cisplatin or DMSO for different time points. Cell viability was detected by MTT assay.

FIG. 3D: An image showing the expression of miR-214 renders A2780S and OV119 cells resistant to cisplatin. After 48 h of the treatment, cells were labeled with Annexin V and analyzed by flow cytometry.

FIG. 4A: An image showing A2780CP, a cisplatin-resistant cell line and expressing elevated levels of endogenous miR-214, was transfected with 2'-O-me-anti-miR-214 or scramble 2'-O-me oligonucleotides and assayed with qRT-PCR with primers of miR-214 (top) and U6 (bottom).

FIG. 4B: An image showing an MTT assay. The 2'-O-me-anti-miR-214- or scramble 2'-O-me-transfected A2780CP cells were treated with 20 uM of cisplatin or DMSO vehicle for the indicated times and examined for cell viability.

FIG. 4C: An image showing flow cytometry. Indicated cells were treated with cisplatin or DMSO for 12 h and the subG1 population was identified by flow cytometry.

FIG. 5A: An image of Topo-miR-214 and vector stably transfected A2780S cells were treated with Akt inhibitor API-2/TCN (10 uM) and/or cisplatin (20 uM). The cells treated with DMSO were used as control. After 24 h of treatment, cells were subjected to immunoblotting analysis with indicated antibodies (upper) and assayed for caspase 3/7 activity (bottom).

FIG. 5B: An image of A2780S cells were stably transfected with indicated plasmids and assayed for expression of PTEN, phospho-Akt-S473 and total Akt (upper). After treatment with or without cisplatin for 24 h, cells were examined for caspase 3/7 activity (bottom).

FIG. 5C: An image of LNA-ISH. miR-214 was labeled with digoxigenin-ddUTP using the Dig-3'-end labeling kit (Roche) and hybridized to paraffin sections of normal ovary (panel 2) as well as a patient with primary and recurrent/cisplatin-resistant ovarian serous carcinoma (panels 3 and 4). Panel 1 uses haematoxylin and eosin (HE) staining Unlike normal ovarian surface epithelial cells (panel 2) and primary tumor (panel 3), recurrent/cisplatin-resistant tumor (panel 4) expresses a high level of miR-214.

FIG. 6A: An image showing miR-214 seed sequence (SEQ ID NO:7) matches with 3'UTR of p53 (SEQ ID NO:6).

FIG. 6B: An image showing knockdown of miR-214 induces p53 (middle lane).

FIG. 6C: An image showing the expression of miR-214 reduces p53 protein expression.

FIG. 6D: An image showing miR-214 has no effect on p53 mRNA.

FIG. 10A: An image showing that cells containing miR-214 inhibit apoptosis caused by PARP.

FIG. 10B: An image showing that cells containing miR-214 reduce gamma radiation-inhibited colony formation. As shown in the image, cells containing only the vector were exposed to gamma radition which inhibited colony formation. Cells that contained miR-214 still formed colonies after exposure to gamma radiation.

FIG. 10C: An image of a graph showing that colony formation is inhibited in cells containing only the vector while cells containing miR-214 exhibited colony formation after gamma irradiation.

FIG. 11A: An image showing miR-100 knockdown seed sequence. hsa-miR-100 seed sequence (SEQ ID NO:8) as well as the leading strand of pSuper-miR-100 (SEQ ID NO:9) and the lagging strand of pSuper-miR-100 (SEQ ID NO:10) are shown.

FIG. 11B: An image showing resulting knockdown of miR-100.

FIG. 11C: An image showing protein expression in various cell lines and indicating that OVCAR-8 cells express high levels of miR-100.

FIG. 16A: An image of a heat map representing 515 miRNAs in 4 normal OSEs and 65 tumors.

FIG. 16B: An image of an enlarged version of the dendrogram from FIG. 15A demonstrating the distinct clustering of normal OSE versus tumor cell lines.

FIG. 16C: An image of a heat map representing 515 miRNAs in 4 HIOSE and 17 ovarian cancer cell lines.

FIG. 16D: An image of an enlarged version of the dendrogram from FIG. 15C demonstrating the distinct clustering of HIOSE versus cancer cell lines.

FIG. 17A: An image of the results from a Northern blot analysis showing the expression of elevated miRNA.

FIG. 17B: An image of the results from a Northern blot analysis showing the downregulated miRNA in ovarian tumors as compared to normal ovarian surface epithelial (OSE) cells. U6 is the loading control.

FIG. 17C: An image of the results from a Northern blot analysis showing the expression of the indicated miRNAs in ovarian cancer cell lines. HIOSE-MCC6 was used as a control.

FIG. 19A: An image showing the Northern blot analysis of microRNAs in ovarian tumors.

FIG. 19B: An image showing the Northern blot analysis of microRNAs in ovarian cancer cell lines.

FIG. 20A: An image of the microRNA expression signatures in serous cystadenoma and LMP.

FIG. 20B: An image of the microRNA expression signatures in mucinous cystadenoma and LMP.

FIG. 20C: An image of the microRNA expression signatures in serous LMP and carcinoma.

FIG. 20D: An image of the microRNA expression signatures in mucinous LMP and cancer.

DETAILED DESCRIPTION OF THE PREFERRED EMBODIMENT

Figure 1:
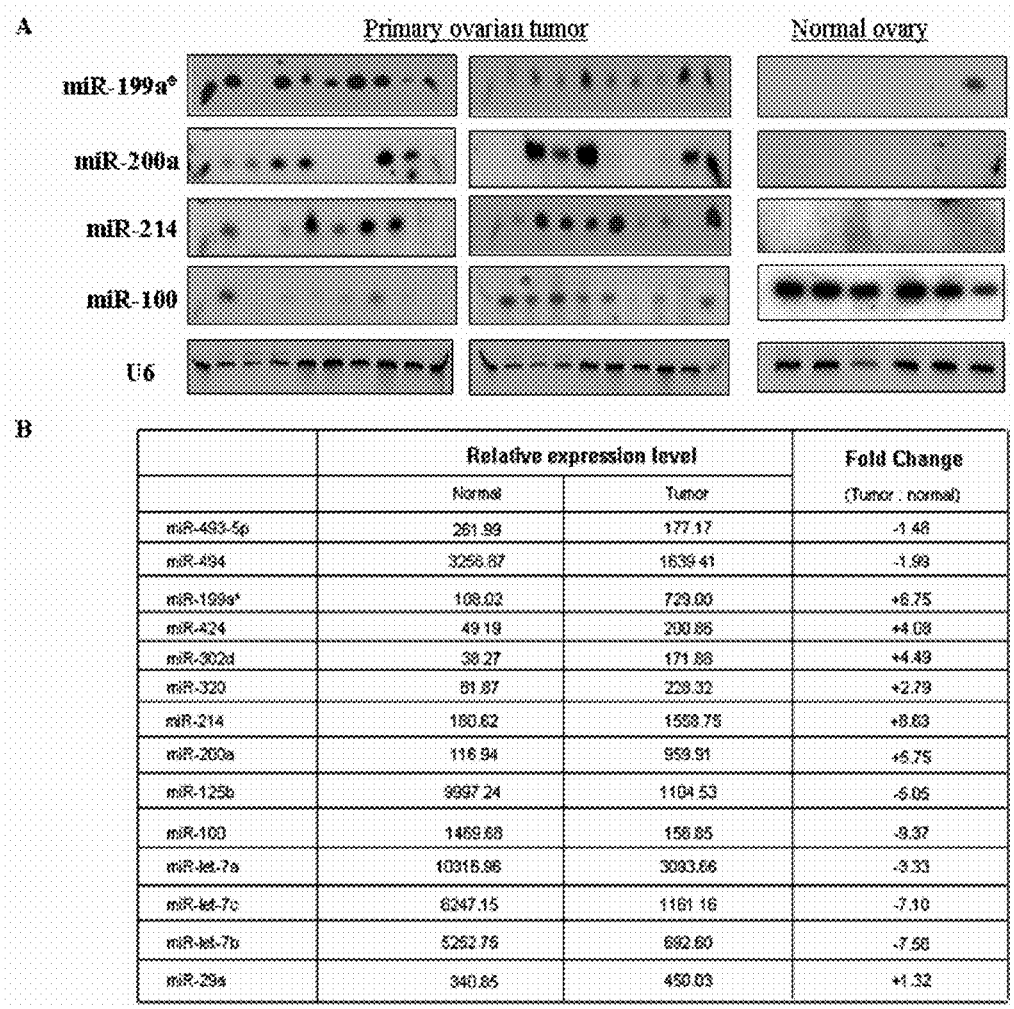
FIG. 1: A series of images showing the miRNA expression profile and frequent deregulation of miR-199*, -200a, -214 and -100 in human primary ovarian cancer.

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

MicroRNAs have been shown to be aberrantly expressed or mutated in human cancer, indicating that they may function as a novel class of oncogenes or tumor suppressor genes. A number of miRNAs were observed deregulated in human ovarian cancer. The aberrant expression of miR-214, -199a*, -200a and -100 was detected in a near or over half of ovarian cancers, especially in late stage and high grade tumors.

Cell Lines and Human Tissue Samples

Human ovarian cancer cell lines and human immortalized ovarian surface epithelial (HIOSE) cell lines were described previously (Yang, H., et al., Aurora-A kinase regulates telomerase activity through c-Myc in human ovarian and breast epithelial cells. Cancer Res. 2004, 64:463-7). HIOSE cells were grown in 199/MDCB 105 (1:1) medium (Sigma) supplemented with 5% fetal bovine serum. Frozen human primary ovarian tumor and normal ovarian tissues were obtained from the Tissue Procurement Facility at H. Lee Moffitt Cancer Center.

MicroRNA Array and Northern Blot Analysis

Oligonucleotide arrays were printed with tri-mer oligonucleotide probes (antisense to miRNAs) specific for 515 human and mouse miRNAs on GeneScreen Plus (NEN) membranes, and miRNA expression profiling was performed and analyzed as previously described (Chan, J., et al., 2005). Briefly, total RNAs were isolated from 10 HIOSE cell lines and 10 primary serous ovarian carcinomas with Trizol reagent (Invitrogen, Carlsbad, Calif.). Low-molecular weight (LMW) RNAs were enriched from total RNAs using Microcon YM-100 columns (Millipore). The LMW RNAs were labeled with [$\gamma$-$^{32}$P]ATP and then hybridized to the miRNA array. To ensure accuracy of the hybridizations, each labeled RNA sample was hybridized with three separate membranes. In addition, eight oligonuclotides with non-matching any known miRNA were used as hybridization controls. Hybridization signals for each spot of the array and background values at 15 empty spots were measured. Raw data were further automatically processed in Microsoft Excel. Hybridization signals that failed to exceed the average background value by more than three standard deviations were excluded from analysis.

For Northern blot analysis, 20 μg of RNA were separated on 15% denaturing polyacrylamide gel and then electroblotted onto a Zeta-Probe GT Blotting Membrane (BioRad). Following transfer, the membrane was dried and UV-crosslinked. The probes were prepared using the Starfire Oligonucleotide Labeling System (Integrated DNA Technologies) according to the manufacturer's protocol. The blots were hybridized overnight at 50° C. in a buffer containing 5×SSC, 20 mM $Na_2HPO_4$ (pH 7.2), 7% SDS, 1×Denhardt's, 0.2 mg/ml salmon sperm DNA, and then washed with 1×SSC/1% SDS buffer at 50° C. (Johnson, S., et al., 2005). The probe sequences are: hsa-miR-199a* 5'-AACCAATGTGCAGACTACTGTA-3'(SEQ ID NO: 11); hsa-miR-214 5'-CTGCCTGTCTGTGCCTGCTGT-3'(SEQ ID NO: 12); hsa-miR-100-5'CAC AAGTTCGGATCTACGGGTT-3' (SEQ ID NO: 13) and hsa-miR-200a 5'-ACATCGTTACCAGACAGTGTTA-3' (SEQ ID NO: 14).

RNase Protection Assay and Quantitative RT-PCR (qRT-PCR)

Expression of miRNAs was also analyzed by RNase protection or mirVana qRT-PCR miRNA detection assay. For RNase protection assay, enriched small RNA was purified using the miRVana miRNA Isolation Kit (Ambion). The mirVana™ miRNA probe construction kit (Ambion) was used to synthesize the $^{32}$P-labeled miR-214 probe. Probe hybridization and RNase protection were then carried out using the mirVana™ miRNA detection kit (Ambion) according to manufacturer's instructions. After hybridization and RNase treatment, the double-strand products were resolved in a 15% polyacrylamide 8 M urea denaturing gel and visualized using phosphoimaging and autoradiography. mirVana qRT-PCR was performed according to the manufacturer's protocol (Ambion). PCR products were analyzed by electrophoresis on a 7.5% polyacrylamide gel in 0.5×TBE and visualized by ethidium bromide staining.

Antisense Inhibition of miRNA Expression

2'-O-methyl (2'-O-me) oligoribonucleotides were synthesized by Integrated DNA Technologies. The sequences of 2'-O-methyl-anti-miR-214 and -miR-199a* are: 5'-CUGC-CUGUCUGUGCCUGCUGU-3' (SEQ ID NO: 1) and 5'-AACCAAUGUGCAGACUAC UGUA-3' (SEQ ID NO: 3). 2'-O-me-scrambled miR (5'-AAAACCUUUUGAC-CGAGCGUGUU-3') (SEQ ID NO: 15) was used as a control. Cells were grown in 6-well plate (1.7×10$^6$ cells/well) for 24 h and transfected with 150 pMol of 2'-O-me oligoribonucleotides per well using Lipofectamine 2000. RNA and protein were extracted after 72 h transfection.

Cloning and Expression of miRNAs

Expression plasmids of miR-214 and -199a* were created by PCR amplification using human genomic DNA as a template. The primers are: miR-214 sense 5'-CACCTTTCTC-CCTTTCCCCTTACTCTCC-3' (SEQ ID NO: 16) and antisense 5'-TTTCAT AGGCACCACTCACTTTAC-3', (SEQ ID NO: 17) and miR-199a* sense 5'-CACCGCCCAGAAG CCACGATCCCAAACC-3' (SEQ ID NO: 18) and antisense: 5'-TGCCTTTCCCCAGTGCCTCTTC TC-3' (SEQ ID NO: 19). The PCR products (392-bp containing pri-miRNA) were cloned into pcDNA3.1/V5-His-TOPO expression vector (Invitrogen) and confirmed by DNA sequencing. The expression of miRNA was carried out by transfection of the plasmid into the cells using Lipofectamine 2000.

Target In Vitro Reporter Assay

For luciferase reporter experiments, the 3' UTR segments of PTEN predicted to interact with miR-214 were amplified by PCR from human genomic DNA and inserted into the Mlu I and Hind III sites of pGL3 vector immediately downstream from the stop codon of luciferase (Promega). A2780CP and HIOSE-80 cells were co-transfected in 12-well plates with 0.4 μg of the firefly luciferase report vector and 0.08 μg of the control vector containing *Renilla* luciferase, pRL-TK (Promega) as well as with or without 0.5 μg of Topo-miR-214. Firefly and *Renilla* luciferase activities were measured consecutively using dual-luciferase assays (Yang, H., et al., 2004).

Cell Viability and Apoptosis Assays

Cell viability was examined with MTT assay as previously described (Yang, L., et al., Akt/protein kinase B signaling inhibitor-2, a selective small molecule inhibitor of Akt signaling with antitumor activity in cancer cells overexpressing Akt. Cancer Res. 2004, 64:4394-9). Apoptosis was detected with annexin V and caspase-3/7 activity (Yuan, Z., et al., AKT2 inhibition of cisplatin-induced JNK/p38 and Bax activation by phosphorylation of ASK1: implication of AKT2 in chemoresistance. J Biol Chem. 2003; 278:23432-40; Yang, L., et al, Akt/protein kinase B, 2004). For detection of caspase-3/7 activity, cells were cultured in 96-well plates and treated with the agents indicated in the figure legends and analyzed using Caspase-Go 3/7 Assay kit (Promega) according to the manufacturer's instructions. Statistical analysis was done using two-sample t test, assuming equal variance, and P value was calculated based on two-tailed test.

miRNA Locked Nucleic Acid In Situ Hybridization (LNA-ISH) of Formalin-Fixed, Paraffin-Embedded (FPPE) Tissue Section.

and downregulated miR-100 (76%, 23/30). Moreover, increased miR-200a was detected in 43% of primary ovarian carcinomas examined (Table 1). Further, while the number of specimens is relatively small, the deregulation of miR-199a*, miR-214 and miR-200a seems to be associated with high grade and late stage tumors (Table 2). These data suggest that alterations of these three miRNAs could be involved in ovarian cancer progression.

TABLE 1

Alterations of miRNA and tumor histopathology.

| Histology | No. | miR-199a* | | miR-214 | | miR-200a | | miR-100 | |
|---|---|---|---|---|---|---|---|---|---|
| | | Low/no | High* | Low/no | High | Low/no | High | Normal | Down |
| Serous cystadenocacinoma | 14 | 5 | 9 | 4 | 10 | 8 | 6 | 6 | 8 |
| Mucinous cystadenocar. | 6 | 2 | 4 | 2 | 4 | 3 | 3 | 1 | 5 |
| Endometrioid carcinoma | 5 | 3 | 2 | 3 | 2 | 3 | 2 | 0 | 5 |
| Clear cell cystadenocar. | 1 | 1 | 0 | 0 | 1 | 1 | 0 | 0 | 1 |
| Granulosa cell tumor | 3 | 2 | 1 | 3 | 0 | 2 | 1 | 0 | 3 |
| Mixed tumor | 1 | 1 | 0 | 1 | 0 | 0 | 1 | 0 | 1 |
| Normal ovary | 10 | 10 | 0 | 10 | 0 | 10 | 0 | 10 | 0 |

A miRNA LNA probe was prepared by 3'-end labeling with digoxigenin-ddUTP-terminal transferase using the Dig-3'-end labeling kit (Roche). Following deparaffinization and proteinase-K digestion, slides were prehybridized for 1 h and then hybridized with 10 nM miRNA LNA probe in a hybridization buffer (Roche) for 12 h. After three consecutive washes in 4×SSC/50% formamide, 2×SSC and 0.1×SSC, sections were treated with a blocking buffer (Roche) for 1 h and incubated with anti-DIG-AP FAB fragments (Roche) for 12 h. Following wash for 3 times in 1× maleic acid and 0.3% Tween-20 buffer, reactions were detected in a detection solution (100 mM tris HCl pH 9.5, and 100 mM NaCl) in the presence of NBT and BCIP (Promega) and then visualized under a microscope.

Frequent deregulation of miR-199a*, -214, -200a and -100 in human ovarian cancer.

miRNA profiles have been reported in different types of tumors derived from different organs, including ovarian cancer. However, the frequency and pathobiological significance of aberrant miRNA expression in human ovarian cancer have not been well documented. miRNA expression was initially analyzed in 10 human ovarian epithelial tumors and 10 "normal" HIOSE cell line pools by hybridization of the array containing 515 miRNAs. After normalization of control oligos, the differential expression of miRNAs between ovarian tumors and normal ovarian surface epithelial cells was quantified using a Phosphorimager. Thirty-six of the 515 miRNAs showed differential expression with P values derived from the nonparametric Wilcoxon/Kruskal-Wallis test being <0.05. Of them, 14 miRNAs that changed more than 1 fold were confirmed by Northern and/or qRT-PCR analysis (FIGS. 1A, 1B and data not shown). To further validate the results, miR-199a*, miR-214, miR-200a and miR-100, 4 of the most differentially expressed miRNAs, were analyzed in 30 primary ovarian cancers (Table 1). As compared to normal ovarian cells, more than half of the primary tumors exhibited elevated levels of miR-199a* (53%, 16/30) and miR-214 (56%; 17/30)

Intensity of signals is ≥2 fold as compared to that of normal ovary and/or HIOSE cells.

The miR-214 targets PTEN leading to activation of the Akt pathway.

Since miR-214 was one of the most frequently up-regulated miRNAs in the ovarian tumors (Table 2 and FIG. 1) and has recently been shown to play an important role in Zebrafish muscle development (Flynt, A., et al., Zebrafish miR-214 modulates Hedgehog signaling to specify muscle cell fate. Nat Genet. 2007, 39:259-63), potential targets of miR-214 were examined by searching the PicTar and miRBase database as well as sequence alignment analysis using GCG Version 11.1. Among the candidates targeted, 3'UTR of human PTEN contains a putative region (nucleotides 3257-3264, NM_000314) that matches to the seed sequence of hsa-miR-214, which is also conserved in mouse and rat (FIG. 2A). To examine whether PTEN is indeed the target of miR-214, a miR-214-negative cell line HIOSE-80 (FIGS. 2B and 3A) was transfected with pcDNA3.1N5-His-Topo-miR-214. The cells transfected with pcDNA3.1N5-His-Topo vector alone and pcDNA3.1N5-His-Topo-miR-199a* were used as controls. Immunoblotting and RT-PCR analyses revealed that PTEN protein but not mRNA was considerably decreased in miR-214-transfected HIOSE-80 cells (FIG. 2B). In contrast, knockdown of miR-214 by 2'-O-methyl miR-214 in A2780CP cells, which express high levels of endogenous miR-214 (FIG. 3A), increased the protein level of PTEN (FIG. 2B). Further, the phosphorylation levels of Akt, a major target of PTEN (Testa J., Bellacosa, A., AKT plays a central role in tumorigenesis. Proc Natl Acad Sci USA. 2001, 98:10983-5), and Akt substrates GSK3β and p70S6K were elevated by ectopic expression of miR-214 and decreased by knockdown of miR-214 (FIG. 2B), suggesting that miR-214 targets the PTEN/Akt pathway.

TABLE 2 miRNA expression level and tumor grade, clinical stage.

| | | No. | miR-199a* | | | miR-214 | | | miR-200a | | | miR-100 | | |
|---|---|---|---|---|---|---|---|---|---|---|---|---|---|---|
| | | | Low/no | High | P value | Low/no | High | P value | Low/no | High | P value | Normal | Down | P value |
| Grade | I-II | 13 | 10 | 3 | 0.004 | 9 | 4 | 0.012 | 10 | 3 | 0.01 | 4 | 9 | 0.39 |
| | III | 17 | 4 | 13 | | 4 | 13 | | 5 | 12 | | 3 | 14 | |
| Stage | I-II | 12 | 9 | 3 | 0.011 | 7 | 5 | 0.087 | 9 | 3 | 0.049 | 4 | 8 | 0.29 |
| | III-IV | 18 | 5 | 13 | | 6 | 12 | | 8 | 10 | | 3 | 15 | |

To further demonstrate that PTEN is negatively regulated by miR-214, luciferase reporters were constructed with wild-type (pGL3-PTEN-3'UTR) and mutated (pGL3-PTENmut-3'UTR) 3'UTR of PTEN (FIG. 2A). Both the wild-type and the mutant reporters were introduced into A2780CP (miR-214-positive) and HIOSE-80 (miR-214-negative) cells, respectively. Luciferase activity of the wild-type, but not mutant, PTEN-3'UTR reporter was significantly suppressed in miR-214-positive A2780CP cells but not in miR-214-negative HOSE-80 cells. Moreover, ectopic expression of miR-214 in HIOSE-80 cells inhibited the wild-type but not the mutated reporter activity (FIG. 2C).

As miR-214 was observed negatively regulating PTEN in cell culture system, in vivo regulation was tested. Inverse correlation of expression of PTEN and miR-214 was investigated in primary ovarian tumor specimens. Of the 30 primary ovarian tumors examined, 13 exhibited down-regulation of PTEN and 17 had overexpression of miR-214 (Table 1). Among 17 tumors with elevated miR-214, 11 (65%) had decreased PTEN levels (FIG. 2D; P<0.0001). These data further support the findings of that the PTEN is a direct target of miR-214.

miR-214 is an anti-apoptotic factor that is associated with cisplatin resistance.

Figure 3:
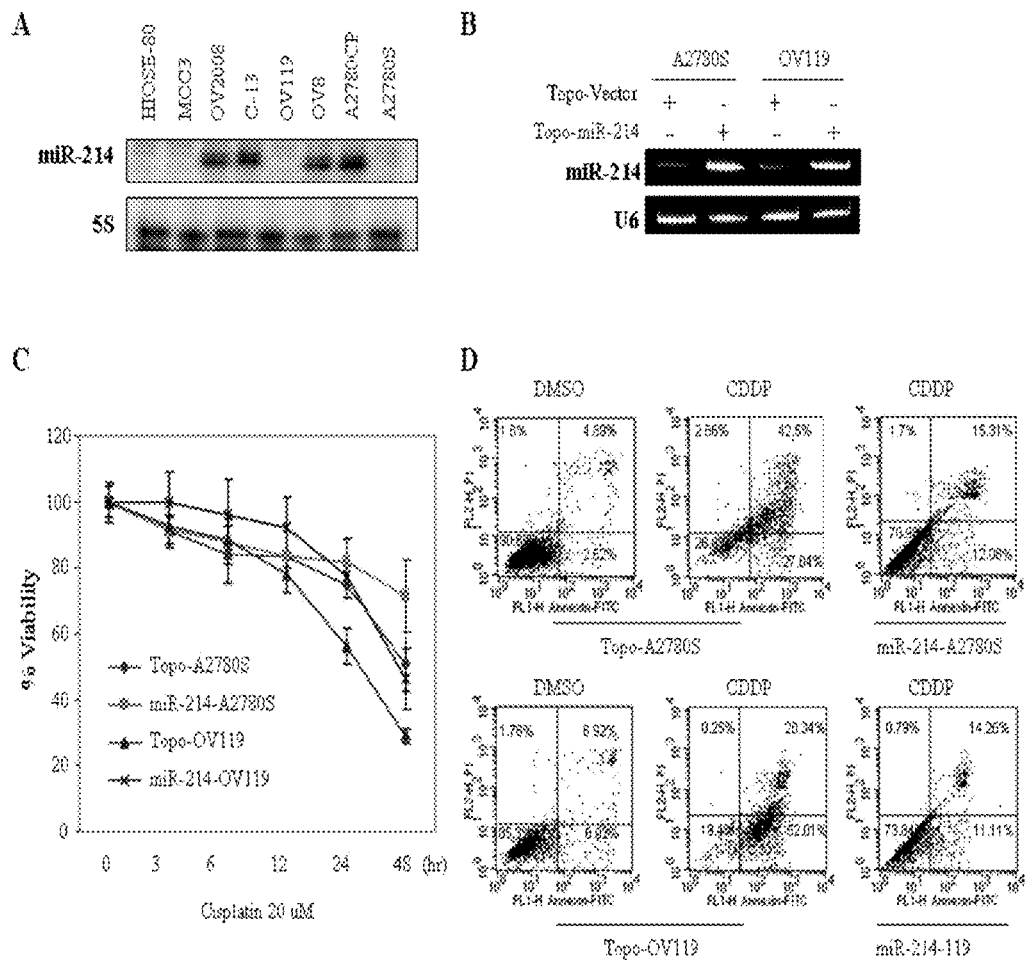
FIG. 3: A series of images showing ectopic expression of miR-214 induces ovarian cancer cells resistant to cisplatin-induced apoptosis.

Since Akt is a major cell survival pathway and its activation plays a key role in multiple drug resistance including cisplatin (Testa, J., 2001), the effects of miR-214 were examined for cell survival and cisplatin resistance. FIG. 3A shows that expression levels of miR-214 are low in immortalized human surface epithelial cell lines, HIOSE-80 and MCC-3 as well as A2780S and OV119 cells as compared to other ovarian cancer cell lines examined. Since A2780S and OV119 cells are sensitive to cisplatin (Yan, X., et al., Over-expression of PTEN sensitizes human ovarian cancer cells to cisplatin-induced apoptosis in a p53-dependent manner. Gynecol Oncol. 2006, 102:348-55), we ectopically expressed miR-214 in these 2 cell lines and examined if expression of miR-214 renders the cells resistant to cisplatin-induced cell death. Following the transfection of pcDNA3.1N5-His-Topo-miR-214 and G418 selection, stable pool cells were obtained and the expression of miR-214 was confirmed by qRT-PCR (FIG. 3B). The cells transfected with miR-214 and pcDNA3.1N5-His-Topo vector were treated with cisplatin or vehicle DMSO. As shown in FIGS. 3C and 3D, the expression of miR-214 confers the cells resistant to cisplatin-induced cell death, suggesting that miR-214 is an anti-apoptotic factor.

Figure 4:
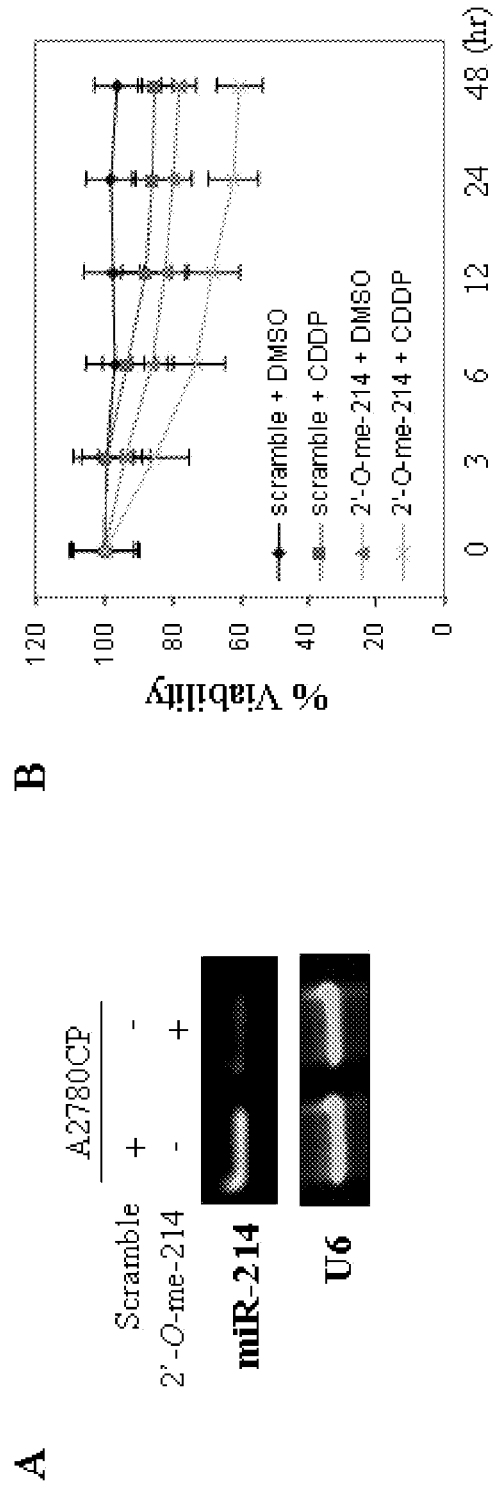
FIG. 4: A series of images showing knockdown of miR-214 sensitizes A2780CP cells to cisplatin.
Figure 4:
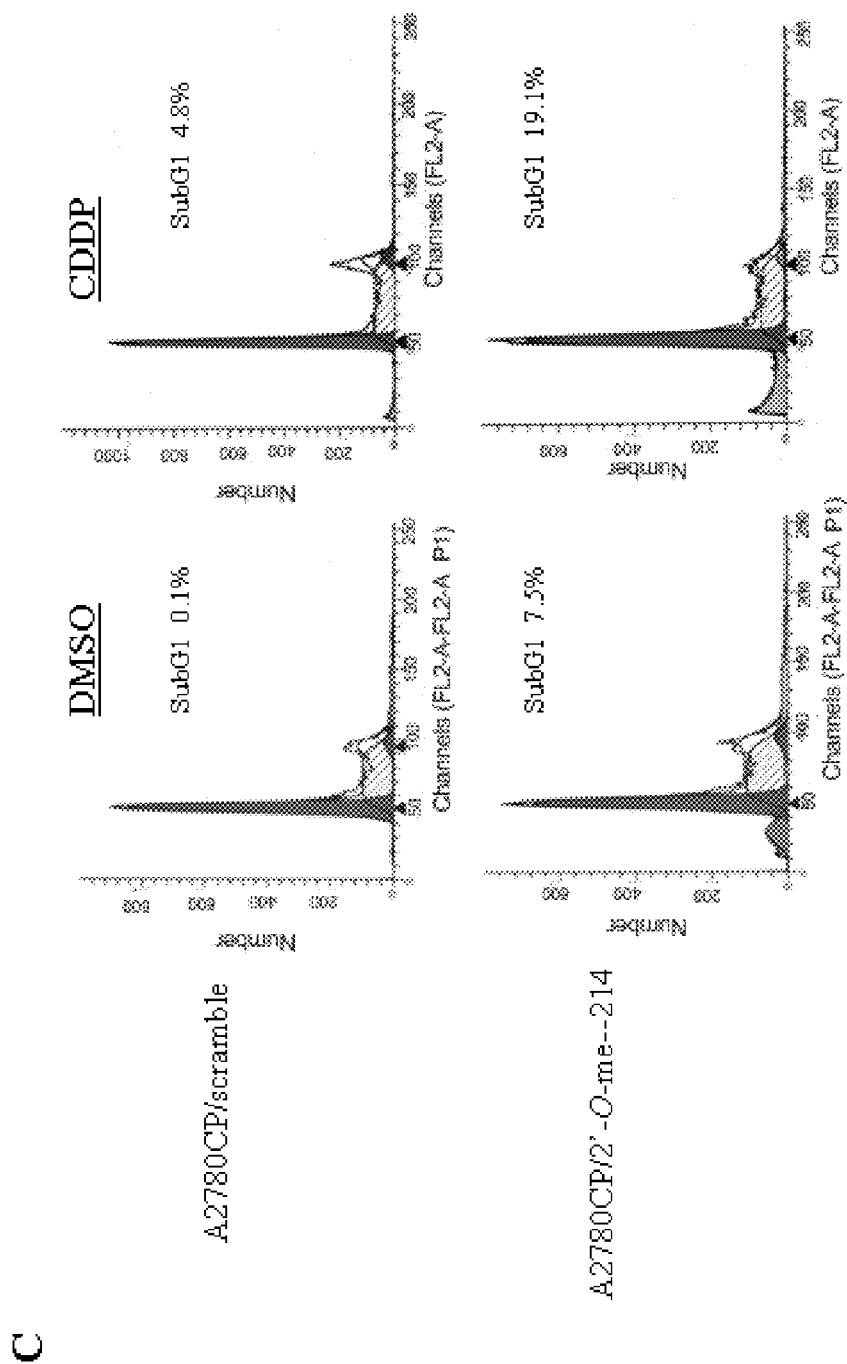

Having demonstrated an elevated level of miR-214 in cis-platin-resistant A2780CP cells (FIG. 3A), knockdown was examined to determine if miR-214 is able to override cisplatin resistance. A2780CP cells were transfected with 2'-O-methyl-anti-miR-214. The cells transfected with 2'-O-methyl-scramble-miR were used as control. Following 72 h transfection, qRT-PCR analysis showed that level of miR-214 was significantly decreased in the cells treated with 2'-O-methyl-anti-miR-214 (FIG. 4A). Further, the cells were treated with cisplatin or vehicle DMSO. Cell viability analysis revealed that knockdown of miR-214 alone reduced cell survival about 20% in A2780CP cells. Moreover, blocking miR-214 expression considerably sensitized A2780CP cells to cisplatin-induced apoptosis (FIGS. 4B and 4C). Taken collectively, these data indicate that miR-214 could play an important role in cisplatin resistance.

Akt inhibitor, API-2/triciribine/TCN, or introduction of PTEN cDNA lacking 3'-UTR reduces cell survival and CDDP resistance induced by miR-214.

Figure 5:
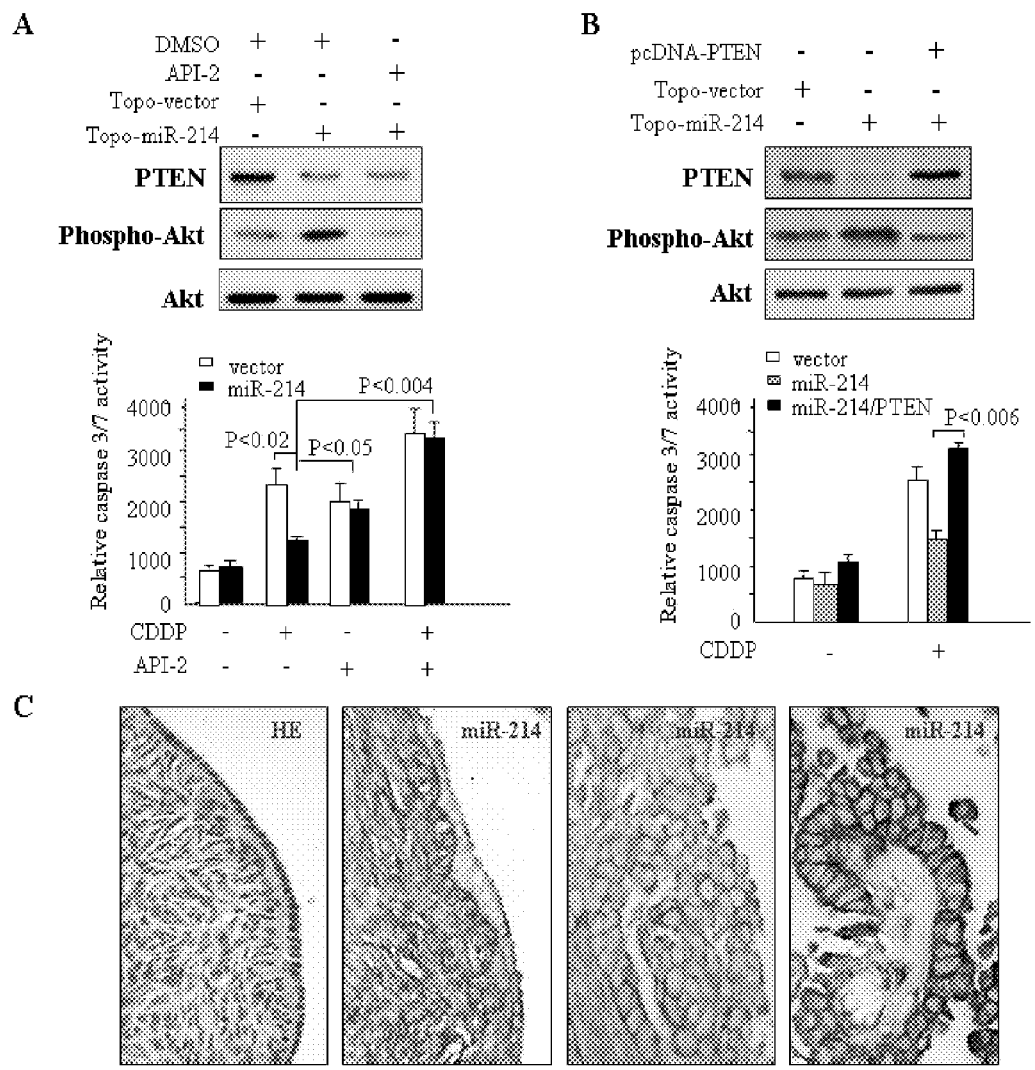
FIG. 5: A series of images showing inhibition of Akt or transfection of PTEN-cDNA lacking 3'UTR overrides miR-214-induced cell survival.

Since ectopic expression of miR-214 reduces PTEN expression leading to activation of Akt pathway (FIGS. 2B and 2C) and inhibition of the cisplatin-induced cell death (FIGS. 3C and 3D), Akt should override miR-214-induced cell survival and cisplatin resistance. A specific, previously identified Akt inhibitor, API-2/TCN, which is currently in clinic trail (Testa, J. 2001; Yang, L., et al., Akt/protein kinase B 2004) was used. miR-2/4-transfected A2780S cells were treated with API-2/TCN, in combination with or without cisplatin. The cells transfected with Topo-vector were used as control. As shown in FIG. 5A, API-2 abrogated miR-214-activated Akt and significantly inhibited miR-214-induced cell survival and cisplatin resistance.

It has been documented that miRNAs negatively regulate the expression of their targets primarily through base-pairing interactions in the mRNA 3' UTR, leading to mRNA degradation or translational inhibition which depends on whether it is partially matched or completely matched with the target genes. Since miR-214 downregulates PTEN through binding to 3'UTR of PTEN mRNA (FIG. 2), ectopic expression of PTEN by transfection of the cDNA that only contains the coding region of PTEN should escape the regulation by miR-214, and thus attenuate or decrease miR-214 function. To this end, pcDNA-PTEN lacking 3'UTR was introduced into miR-214-transfected A2780S cells and then treated with or without cisplatin for 24 h. As shown in FIG. 5B, expression of PTEN decreased Akt activation induced by miR-214 and sensitized the miR-214-A2780S cells to cisplatin-induced apoptosis. These results further indicate that the PTEN/Akt pathway is a major target of miR-214 and largely mediates miR-214 anti-apoptotic function.

While adjuvant chemotherapy with cisplatin achieves clinical response in approximately 80% of patients, the tumor recurs in most patients within 3 years following treatment due to the development of chemoresistance (Aghajanian, C. Clinical update: novel targets in gynecologic malignancies. Semin Oncol. 2004. 31:22-6). Having demonstrated that miR-214 is involved in cisplatin resistance in ovarian cancer cell lines, miR-214 was examined to determine its involvement in cisplatin resistance in patients with ovarian cancer (e.g., more frequent overexpression in chemoresistant/recurrent tumors than in sensitive/primary lesions). Among 30 primary ovarian tumors examined, 11 patients with recurrent (chemoresistant) ovarian cancer were readmitted at H. Lee Moffitt Cancer Center: MiRNA locked nucleic acid in situ hybridization (LNA-ISH) analysis revealed that miR-214 levels were low or undetectable in 8 primary tumors but elevated in their recurrent lesions (FIG. 5C and data not shown). The remaining tumors expressed high level of miR-214 in both primary and recurrent tumors. These data further suggest that miR-214 plays an important role in chemoresistance.

Profiles of miRNA have been reported in different types of human malignancy (Calin G A, et al., 2002; Iorio, M., et al., 2005; Zhang L, et al., 2006; Lu, J., et al., 2005; Chan, J., et al., 2005; Takamizawa, J., et al., 2004; He, H., et al. 2005; Volinia, S., et al., 2006; Lee, E., et al., 2007; Gaur, A., et al. 2007). Thus far, there is a miRNA DNA copy number study of human ovarian cancer in combination with breast cancer and melanoma using high-resolution array-based comparative genomic hybridization. In this study, a high proportion of genomic loci containing miRNA genes exhibited DNA copy number alterations in ovarian and breast cancers and melanoma (Zhang L, et al., 2006). miRNA expression profiling was performed in "normal" HIOSE and epithelial ovarian carcinomas and demonstrated that up-regulation of miR-214, -199a* and -200a and down-regulation of miR-100 are recurrent events and that alterations of the first 3 miRNAs appear to be associated with late stage and high grade ovarian tumors (Table 2). This finding suggests that deregulation of miR-214, -199a* and -200a could contribute to ovarian tumor progression rather than initiation.

While members of the let-7 family, miR-21, -145, -221 and -155 are often deregulated in several cancers including carcinomas of breast, lung and colon (Negrini, M., et al., MicroRNAs in human cancer: from research to therapy. J Cell Sci. 2007, 120:1833-40), there are miRNAs deregulated in specific neoplasms. For example, miR-122a, a liver-specific miRNA, is downregulated in hepatocellular carcinoma (Kutay, H., et al., Downregulation of miR-122 in the rodent and human hepatocellular carcinomas. J. Cell. Biochem. 2006, 99:671-8); miR-204 and miR-211 are upregulated in insulinomas (Roldo C, et al., MicroRNA expression abnormalities in pancreatic endocrine and acinar tumors are associated with distinctive pathologic features and clinical behavior. J. Clin. Oncol. 2006, 24:4677-84). Accumulated evidence shows that miRNA expression signatures correlate well with specific clinical cancer characteristics and can be used to classify normal and cancerous tissues as well as subtype of malignancy (Cummins, J., Velculescu, V., Implications of micro-RNA profiling for cancer diagnosis. Oncogene. 2006, 25:6220-7; Dalmay, T., Edwards, D., MicroRNAs and the hallmarks of cancer. Oncogene. 2006, 25:6170-5; Tricoli, J., Jacobson, J., MicroRNA: Potential for Cancer Detection, Diagnosis, and Prognosis. Cancer Res. 2007, 67:4553-5). Therefore, miRNA signatures might be more effective than mRNA signatures in categorizing, detecting and predicting the course of human cancers as well as in characterizing developmental origins of tumors (Tricoli, J., 2007). The study demonstrated different expression patterns of miRNAs between ovarian cancer and "normal" HIOSE cells. While deregulation of let-7, miR-100, -214, -200a and -125 has been detected in other tumors, alterations of other miRNAs, including miR-424 and miR-494, were only observed in ovarian cancer. Further investigation is required for evaluating these miRNAs as specific markers in ovarian tumors.

Figure 2:
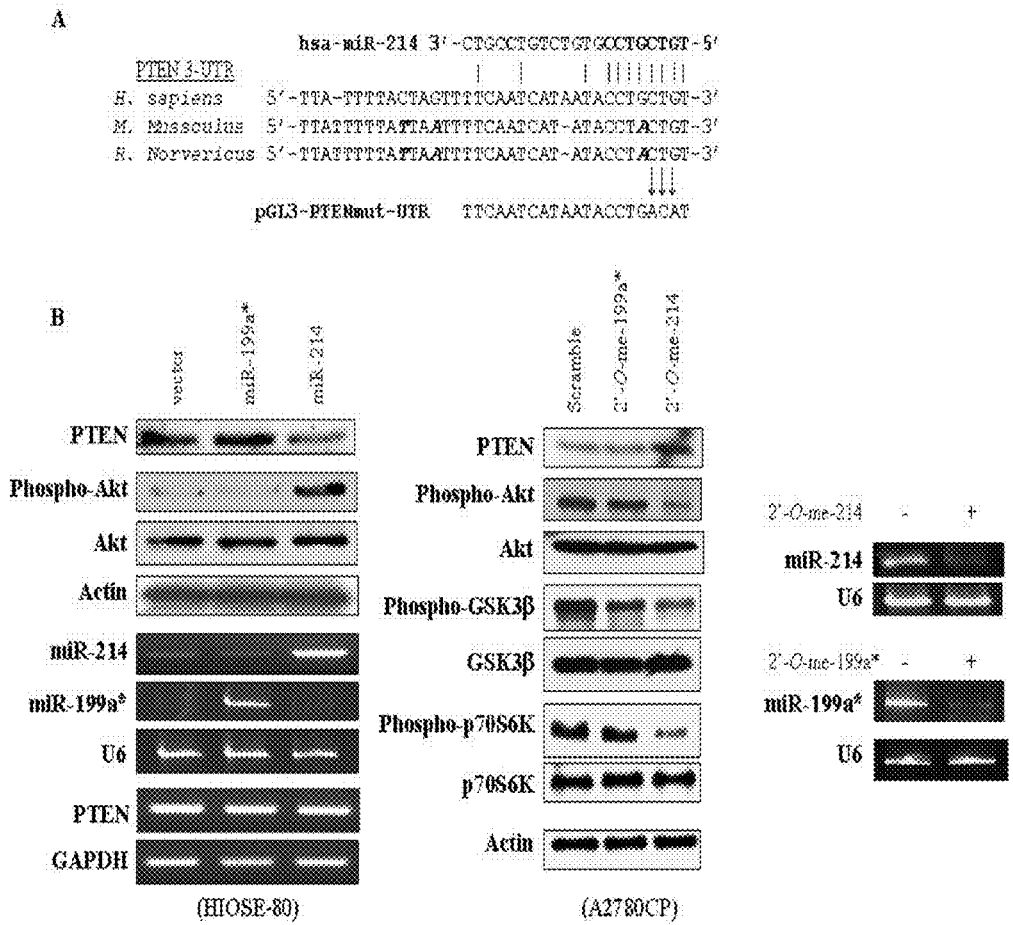
FIG. 2: A series of images showing miR-214 negatively regulates PTEN through binding to 3'UTR of the PTEN.
Figure 2:
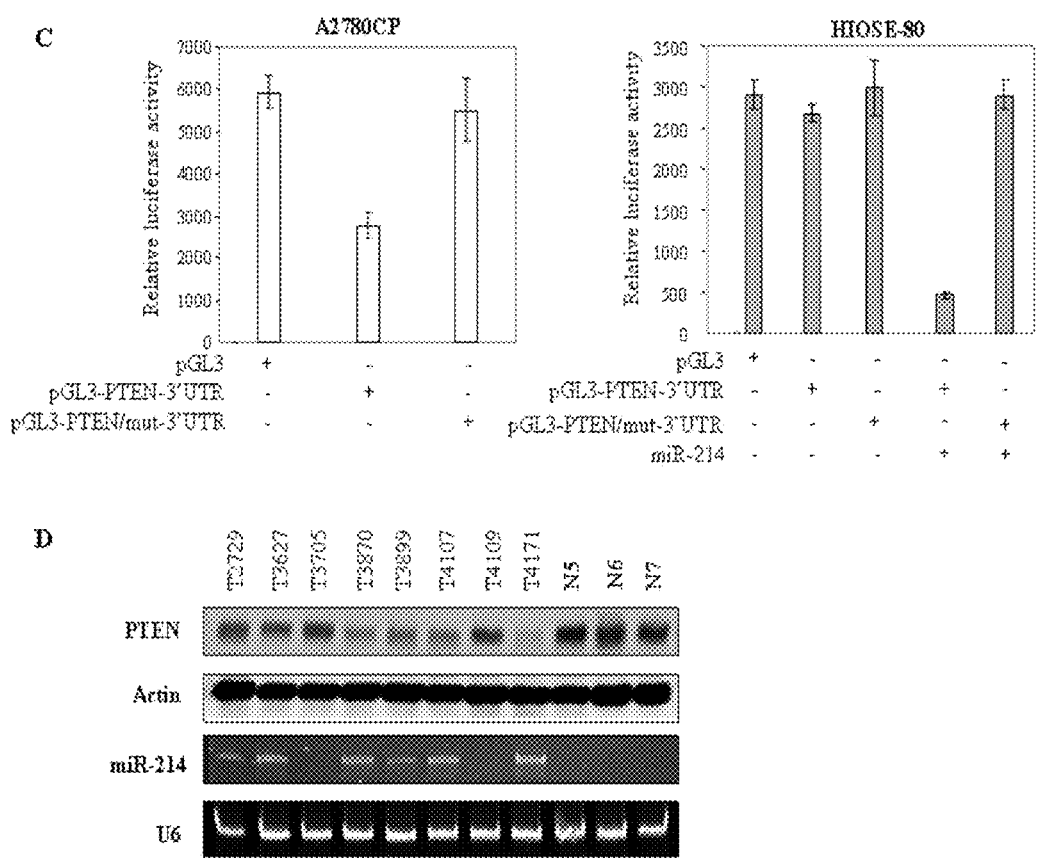

Previous studies have shown that miRNA could serve as "oncogene" or "tumor suppressor gene" and regulate different cellular processes by targeting hundreds of genes. miR-214 is now shown to be highly expressed in the cisplatin-resistant A2780CP cell line as compared to its corresponding cisplatin-sensitive cell line A2780S. Knockdown of miR-214 overrides cisplatin resistance in A2780CP cells, whereas ectopic expression of miR-214 renders A2780S and OV119 cells resistant to cisplatin-induced apoptosis. It has been well documented that constitutive activation of Akt contributes to chemoresistance in different types of tumors including ovarian carcinoma (Testa, J., 2001). miR-214 blocks PTEN translation leading to activation of the Akt pathway (FIG. 2). These indicate that miR-214 plays an important role in cisplatin resistance by targeting PTEN/Akt pathway. While alterations of a number of oncogenes (e.g., Ras, Src and Bcl2 etc.) and tumor suppressor genes (e.g., p53, RB, and p16 etc.) are closely associated with chemoresistance, the involvement of miRNA in this process has not been documented. Thus, the study provided direct evidence that miRNA is of critical role in chemoresistance of human ovarian cancer.

Figure 6:
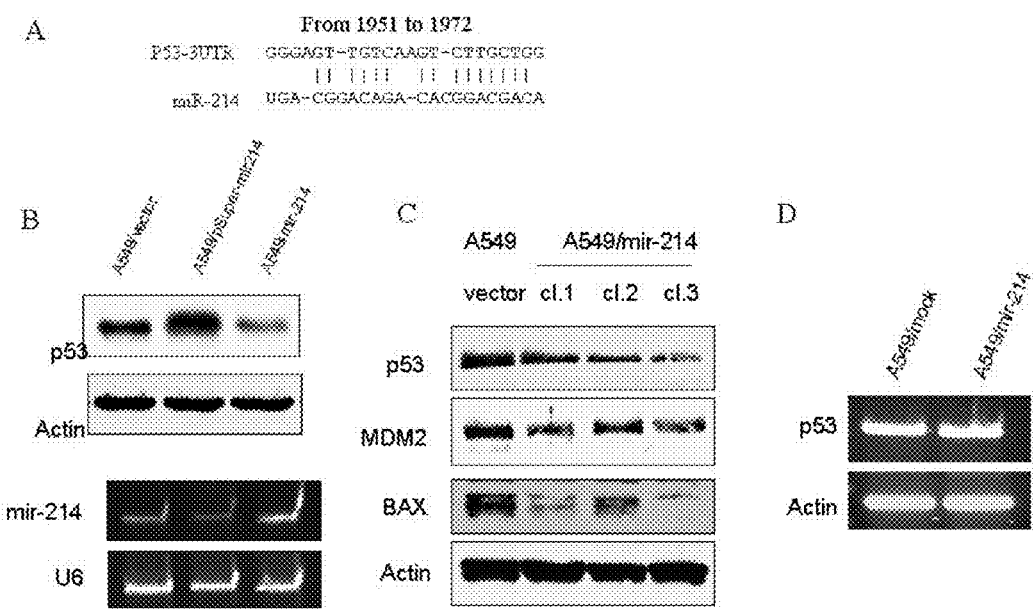
FIG. 6: A series of images showing miR-200a inhibits p53 protein levels.

Mutation of PTEN has been detected only in endometrioid ovarian cancer (Obata, K., et al., Frequent PTEN/MMAC mutations in endometrioid but not serous or mucinous epithelial ovarian tumors. Cancer Res. 1998, 58:2095-7). However, down-regulation of PTEN protein is frequently detected in serous and mucinous epithelial ovarian tumors (Kurose, K., et al., 2001). Frequent loss of PTEN expression is linked to elevated phosphorylated Akt levels, but not associated with p27 and cyclin D1 expression, in primary epithelial ovarian carcinomas. Am J Pathol. 2001, 158:2097-106). The mechanism of down-regulation of PTEN was thought to be promoter hypermethylation. However, the demethylation agent 5-aza-2' deoxycytidine failed to restore PTEN protein expression, suggesting that PTEN is highly regulated at the translational level and that methylation of the PTEN gene plays a subordinate role in ovarian cancer (Schondorf, T., et al., Hypermethylation of the PTEN gene in ovarian cancer cell lines. Cancer Lett. 2004, 207:215-20). PTEN was shown negatively regulated by miR-214 at the protein level and that down-regulation of PTEN largely correlates with elevated levels of miR-214 in ovarian cancer (FIG. 2D). Therefore, these data indicate that miR-214 is a causal factor of the down-regulation of PTEN in human ovarian cancer. Moreover, introducing miR-214 in ovarian cancer cells inhibits pro-apoptotic p53, as seen in FIG. 6. Furthermore, knockdown of miR-214 induced p53 expression (FIG. 6B).

Figure 7:
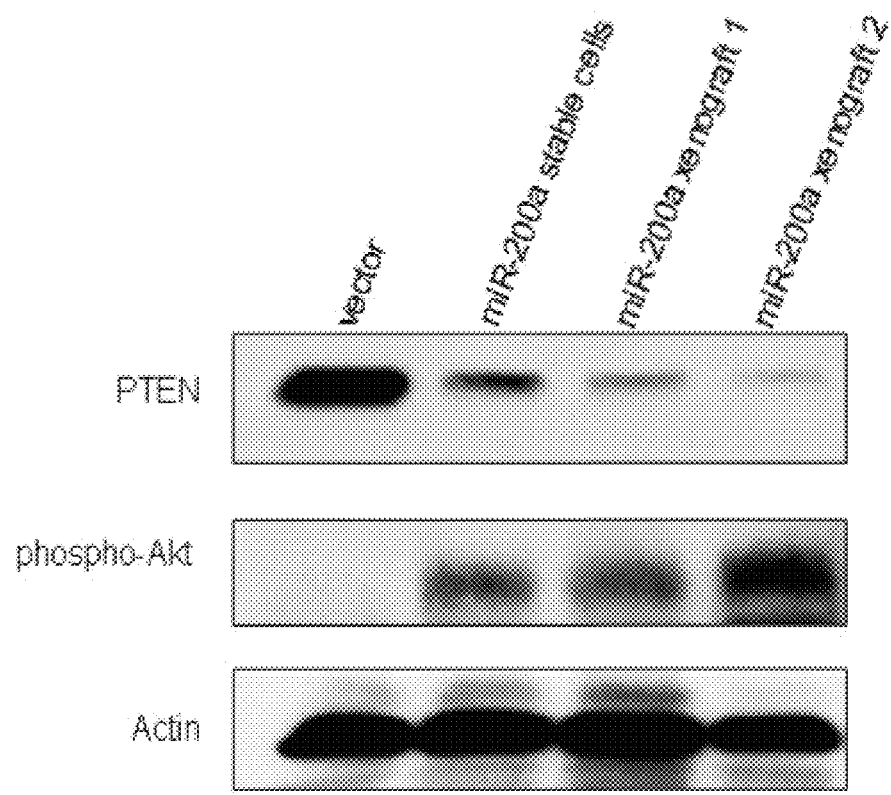
FIG. 7: An image showing miR-200a inhibition of PTEN expression in xenograft mouse model.
Figure 8:
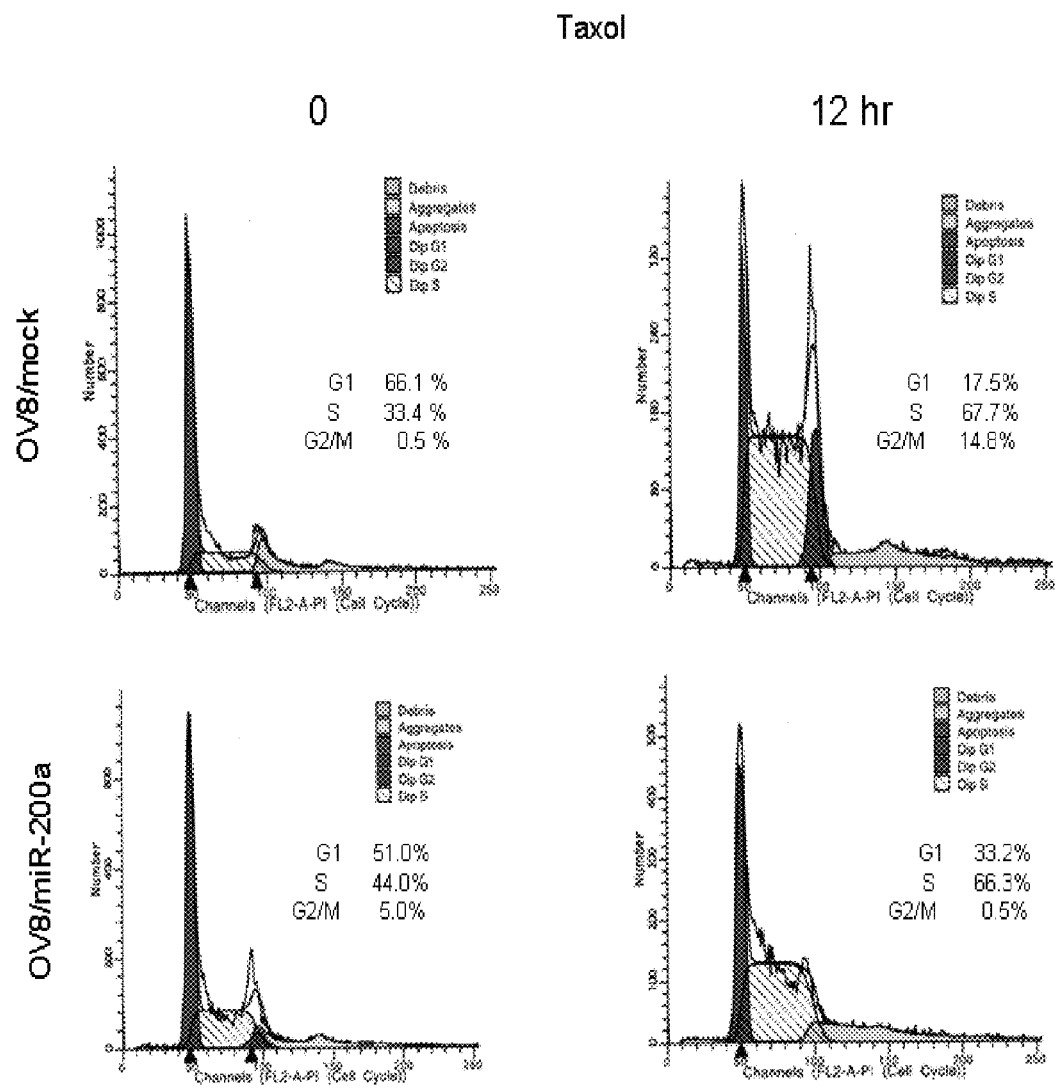
FIG. 8: An image showing expression of miR-200a in OVCAR-8 inhibits taxol-induced G2/M cell cycle arrest.
Figure 9:
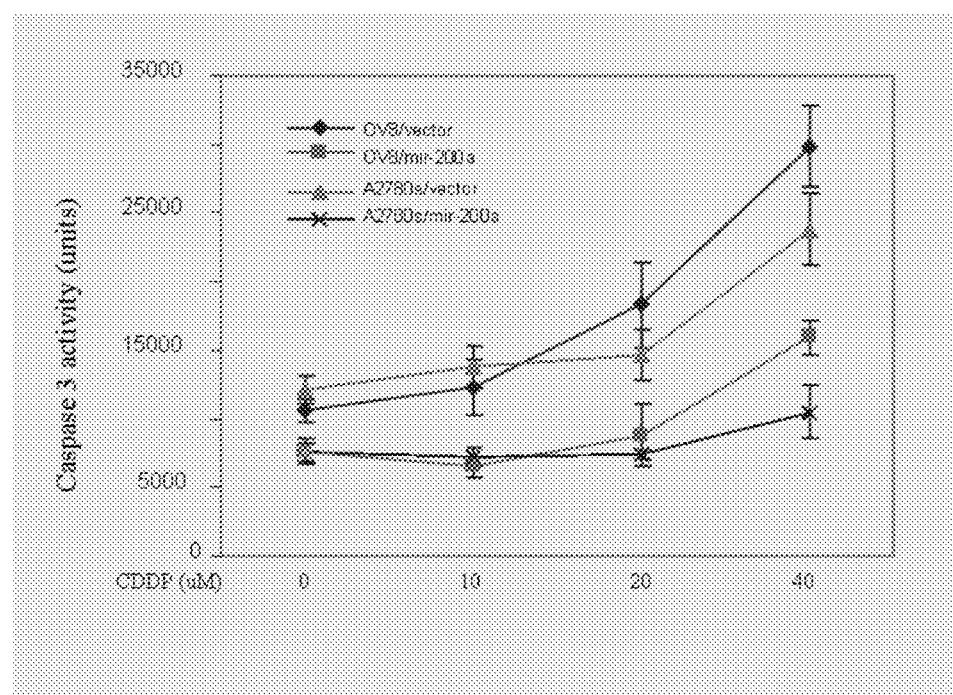
FIG. 9: An image showing miR-200a reduces CDDP-induced apoptosis in OVCAR-8 and A-2780s ovarian cancer cells.
Figure 10:
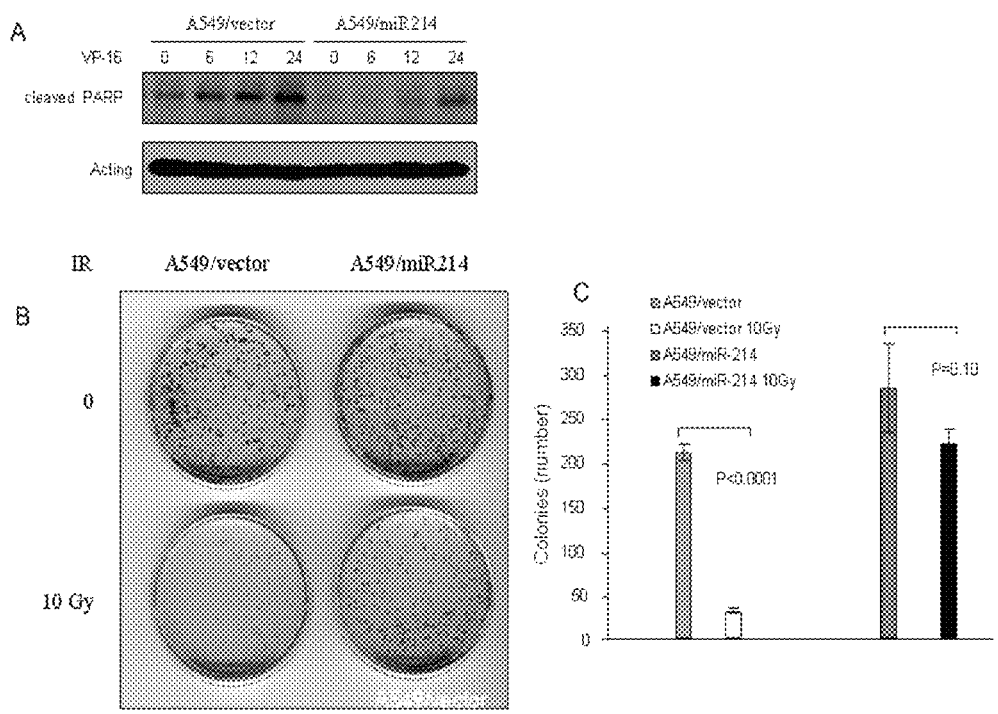
FIG. 10: A series of images showing expression of miR-214 reduces gamma radiation-inhibited colony formation.
Figure 11:
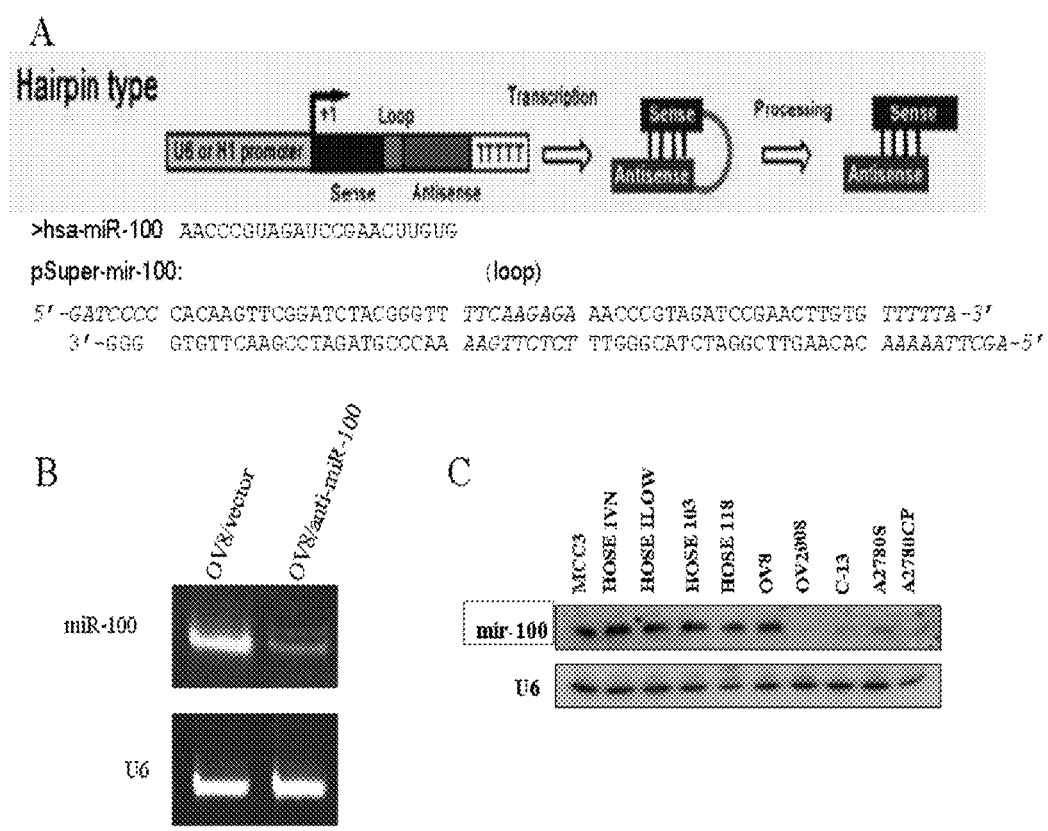
FIG. 11: A series of images showing stable knockdown of miR-100 in OVCAR-8 cells.
Figure 12:
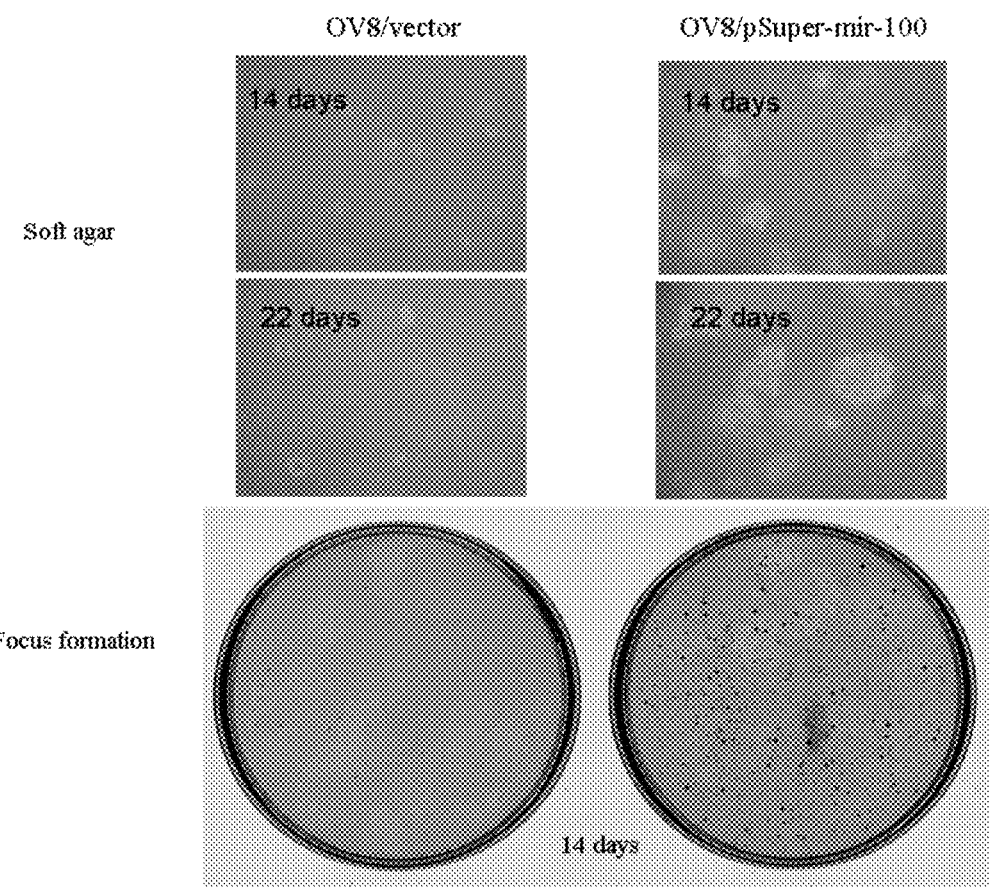
FIG. 12: An image showing knockdown of miR-100 enhances colony (upper) and focus formation.
Figure 13:
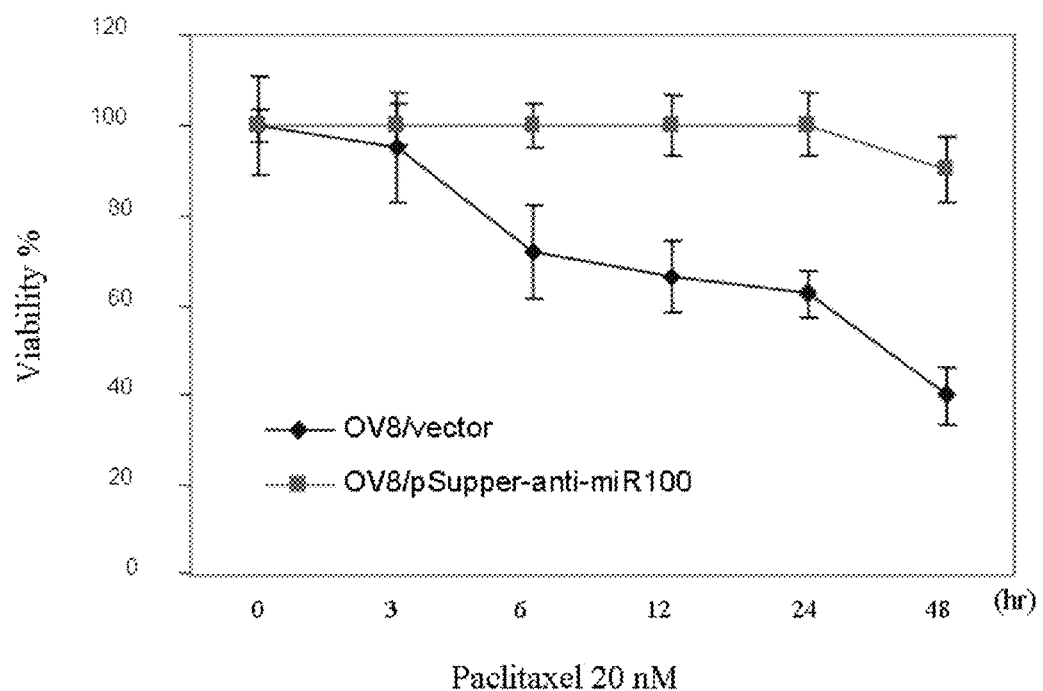
FIG. 13: An image showing down-regulation of miR-100 sensitizes cells to taxol-induced cell death.
Figure 14:
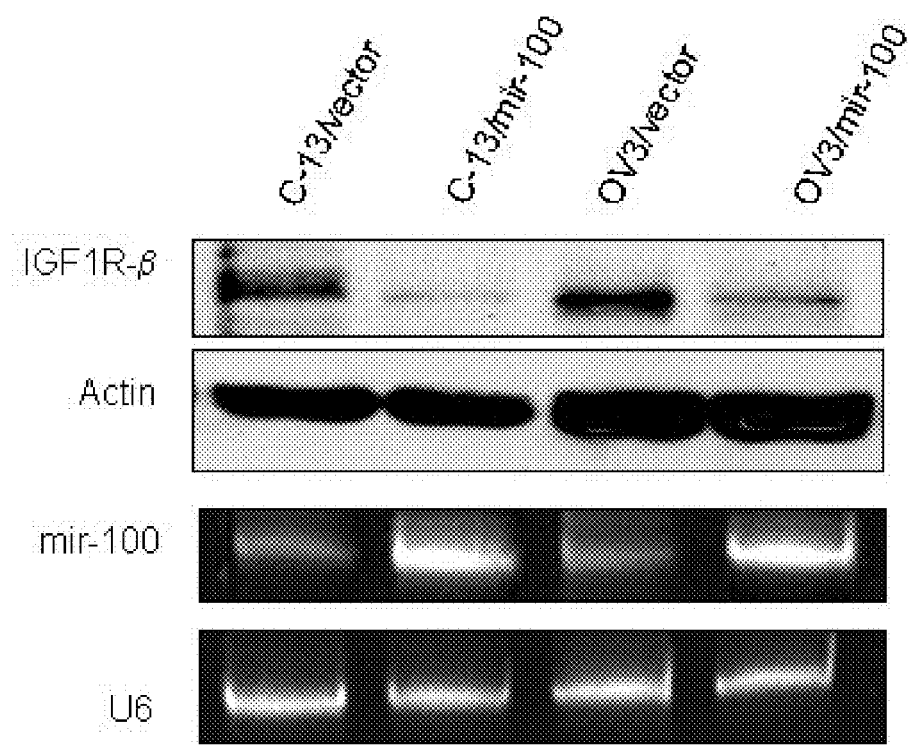
FIG. 14: An image showing miR-100 down-regulation of IGF1 receptor (lanes 2 and 4).
Figure 15:
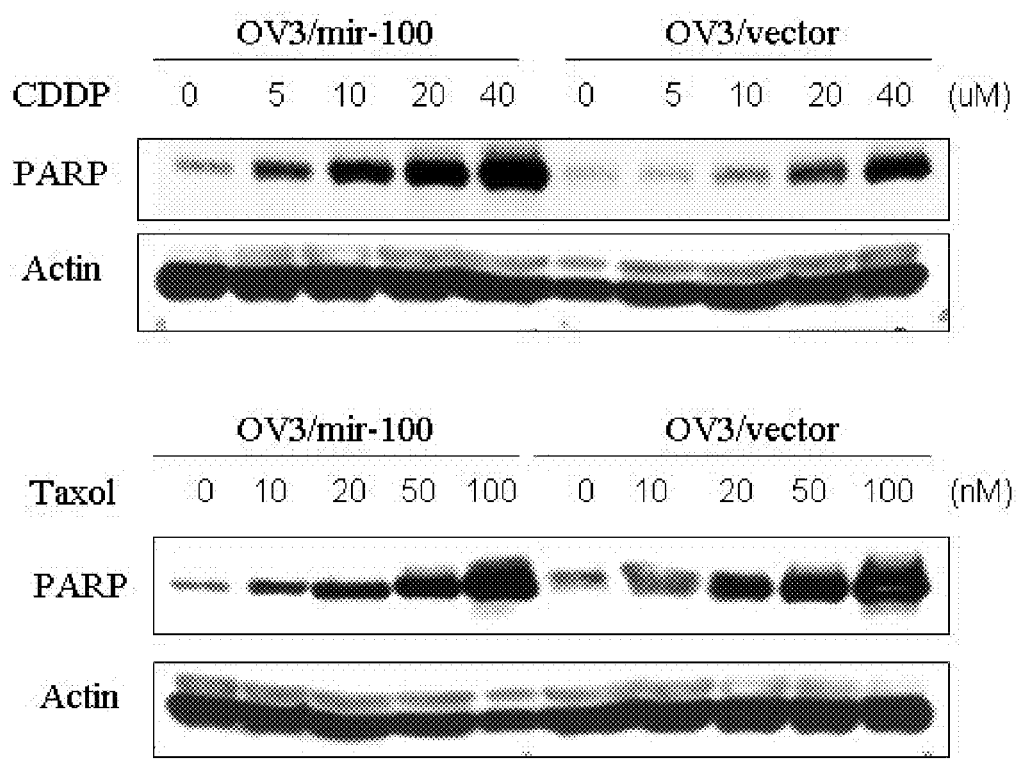
FIG. 15: An image showing a comparison of OV3 cells with miR-100 and without miR-100 exposed to treatment with CDDP or Taxol.

Introducing miR-214 in ovarian cancer cells also reduces gamma radiation inhibition of colony formation, seen in FIG. 10. FIG. 10 provides further evidence that miR-214 is a causal factor of the down-regulation of PTEN in ovarian cancer. Cells containing miR-214 and cells with the vector but no miR-214 were irradiated and the colony formation was observed. It was found that the cells containing miR214 still produced colonies while the cells containing only the vector did not produce colonies after gamma irradiation. Studies of miR-200 in xenograft mouse models also show PTEN-Akt pathways intimately linked to miRNA. Transfection of ovarian cancer miR-200 indicated a dramatic decrease in PTEN protein level, shown in FIG. 7. Further, down-regulation of PTEN correlates with elevated levels of phosphor-Akt, exhibiting an inverse correlation between PTEN and phosphorylated Akt, as modulated by miR-200. The introduction of miR-200 into OVCAR-8 ovarian cancer cells also diminished the antitumor effects of taxol, inhibiting the G2/M cell cycle arrest typically found in taxol-treated cells, as seen in FIG. 8. These results were extended to cisplatin, where miR-200 reduced CDDP-induced apoptosis in various cancer cell lines, seen in FIG. 9. These mi-RNA effects are also seen in miR-100 transfected cells, as seen in FIGS. 11-15.

Deregulation of miR-214, -199a* -200a and -100 is a frequent event in ovarian cancer. Alteration of miR-214, -199a* and -200a seems to be associated with tumor progression. Further, miR-214 induces cell survival and cisplatin resistance by targeting the PTEN/Akt pathway. Therefore, these miRNAs could play an important role in the pathogenesis of this malignancy and are potential targets for ovarian cancer intervention.

Figure 16:
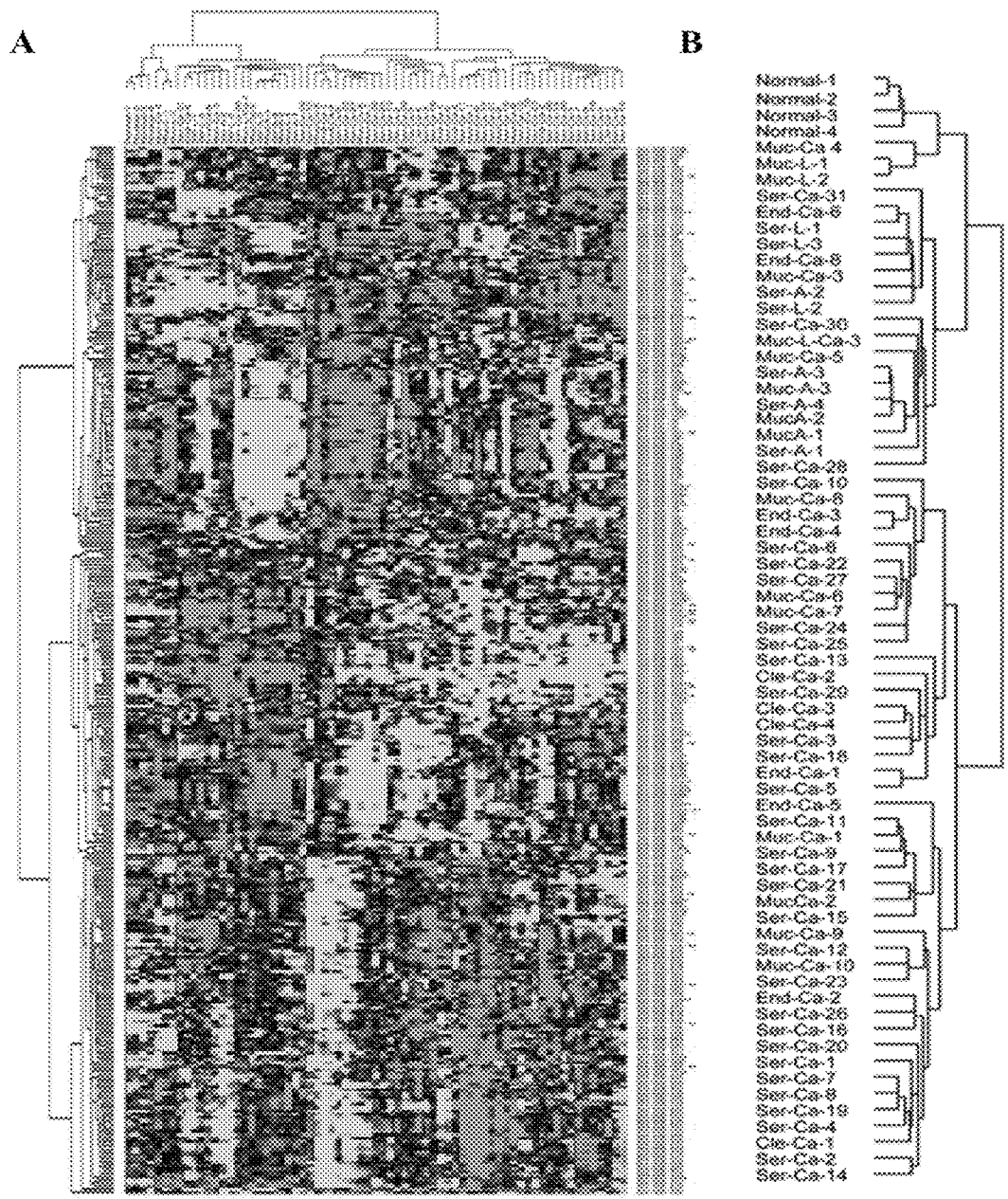
FIG. 16: A series of images showing the miRNA expression patterns distinguishing ovarian tumors and cancer cells from normal OSE and HIOSE cells.
Figure 16:
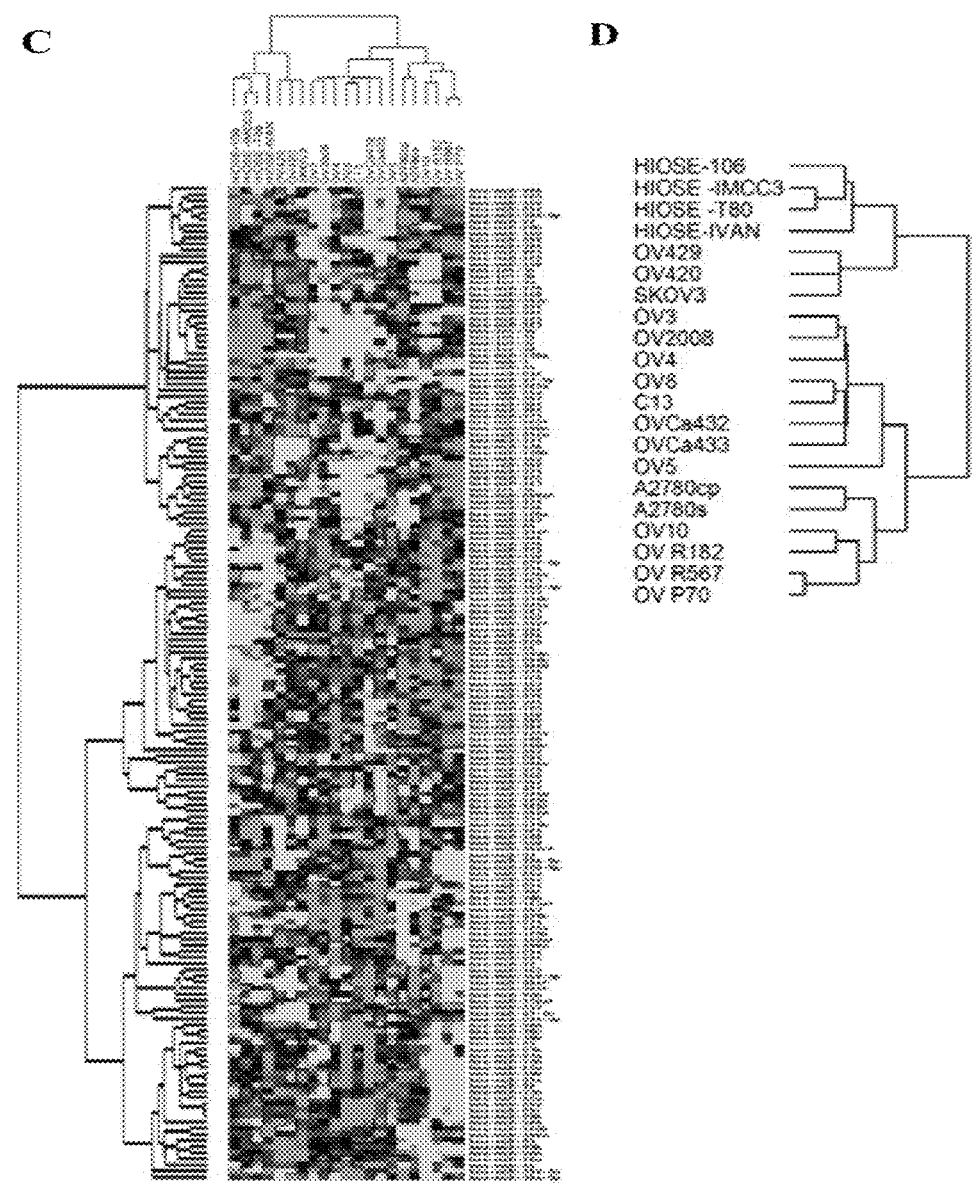

MicroRNA expression patterns distinguish ovarian tumors and cancer cells from normal OSE and HIOSE cells. MicroRNA expression profiles were completed in 65 primary ovarian tumors and 17 ovarian cancer cell lines as seen in FIG. 16. After normalization, 463 and 429 miRNAs were expressed above background levels in 4 pool normal OSE specimens and 4 HIOSE cell lines and were included in subsequent analyses. Hierarchal clustering analysis revealed distinct expression patterns between normal OSEs and primary tumors as seen in FIGS. 16A and 16B as well as between HIOSE cells and all ovarian cancer cell lines, as seen in FIGS. 16C and 16D.

TABLE 3

Top regulated miRNAs in ovarian tumors
Table 3. Top deregulated miRINAs in ovarian tumors

| miRNA | Cluster | Fold change | Concordant in cell lines |
|---|---|---|---|
| miR-214 | 214/199a-2 | 8.5 | Yes |
| miR-200a | 200a/200b/429 | 7.7 | Yes |
| miR-21 | | 7.6 | Yes |
| miR-221 | 221/222 | 3.3 | Yes |
| miR-200c | 200c/141 | 3.3 | Yes |
| miR-7 | | 3.1 | |
| miR-9 | | 2.8 | Yes |
| miR-181a-1 | 181a-1/181b-1 | 2.8 | Yes |
| miR-18a | | 2.7 | |
| miR-429 | 200a/200b/429 | 2.7 | Yes |
| miR-182 | | 2.7 | Yes |
| miR-222 | 221/222 | 2.6 | Yes |
| miR-22 | | 2.6 | Yes |
| miR-200b | 200a/200b/429 | 2.6 | Yes |
| miR-215 | 215/194-1 | 2.6 | |
| miR-199a-2 | 214/199a-2 | 2.5 | Yes |
| miR-181b-1 | 181a-1/181b-1 | 2.2 | Yes |
| miR-194-1 | 215/194-1 | 2.2 | Yes |
| miR-141 | 200c/141 | 2.1 | Yes |
| miR-126 | | −4.7 | Yes |
| Let-7a-2 | Let-7a-2/100 | −4.2 | Yes |
| miR-100 | Let-7a-2/100 | −3.9 | Yes |
| Let-7d | Let-7d/Let-7f-1 | −3.7 | Yes |
| miR-34c | | −3.5 | |
| Let-7f-1 | Let-7d/Let-7f-1 | −3.8 | Yes |
| miR-518e | | −3.6 | Yes |
| miR-299-5p | | −2.1 | |
| miR-93 | | −2.1 | |
| miR-27b | | −3.0 | |
| miR-125b | | −3.8 | Yes |

After quantification and using the t-test procedure within significant analysis of the microarray, we identified a total of 33 miRNAs that are increased or decreased at least two-fold in primary tumors relative to normal OSE controls with P values <0.05. Twenty-three of these are also deregulated in ovarian cancer cell lines. Within this set, we also observed concordant abnormal expression of multiple members of individual miRNA clusters (e.g. miR-214/miR-199a-2, miR-200, -221/-222 and -181 clusters) as seen in Table 3, which are co-regulated. This finding provides an internal indicator of the quality of data generated by out microarray platform.

Figure 17:
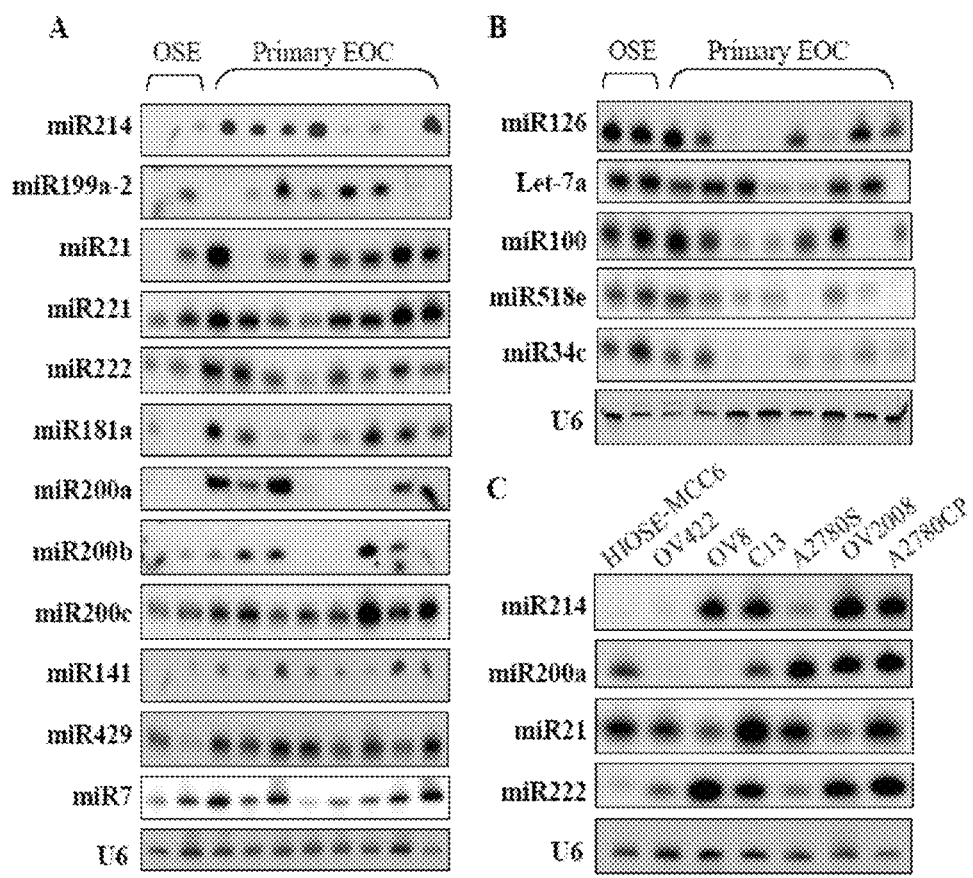
FIG. 17: A series of images validating the miRNA changes.
Figure 18:
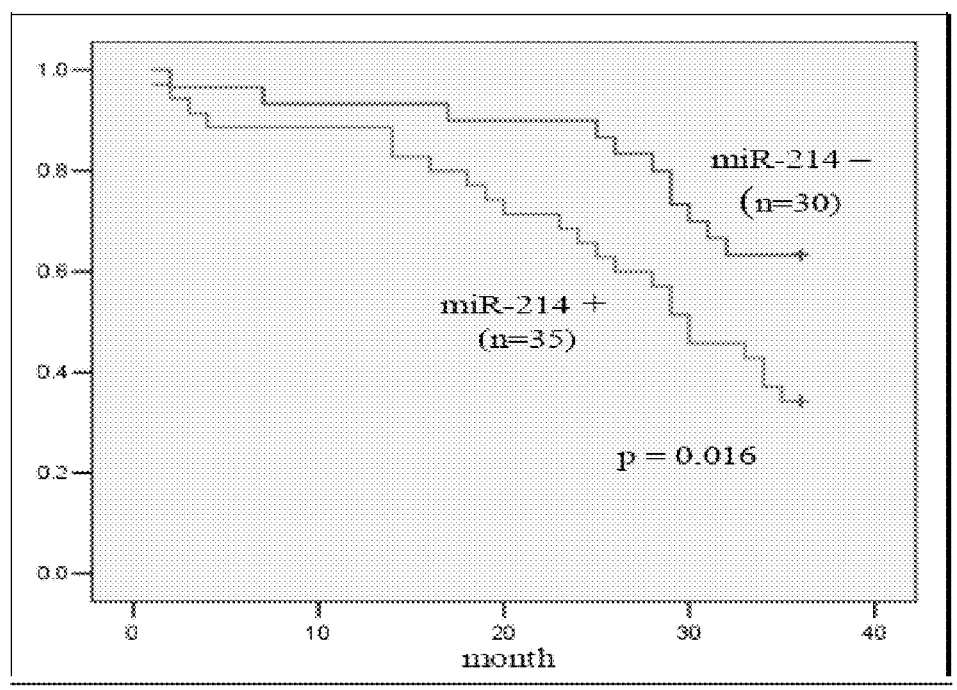
FIG. 18: An image showing the poor prognosis of patients with increased levels of miR-214. Of the 82 ovarian cancers examined, 65 patients had a three-year survival data available. Kaplan-Meier Survival Curve Analysis with the log-rank statistics revealed that the patients with increased levels of miR-214 had poor prognosis as compared to those whose tumors do not express elevated miR-214 which suggests a pivotal role of miRNAs, especially miR-214, in ovarian cancer.

To validate these findings, we performed Northern blot, real-time PCR and miRNA locked nucleic acid in situ hybridization (LNA-ISH) in the primary tumors and/or cells lines as seen in FIG. 17. These results directly paralleled the expression data obtained from the microarray. Further analysis of the top ten deregulated miRNAs in 82 primary ovarian epithelial carcinomas revealed that miR-214 is one of the most frequently elevated miRNAs, especially in late stage and high grade tumors. Of the 82 ovarian cancers examined, 65 patients had three-year survival data available. Kaplan-Meier Survival Curve Analysis with the log-rank statistics revealed that the patients with increased levels of miR-214 has poor prognosis as compared to those whose tumors do not express elevated miR-214, as shown in FIG. 18. These findings indicate a pivotal role for miRNAs, especially miR-214, in ovarian cancer.

Figure 19:
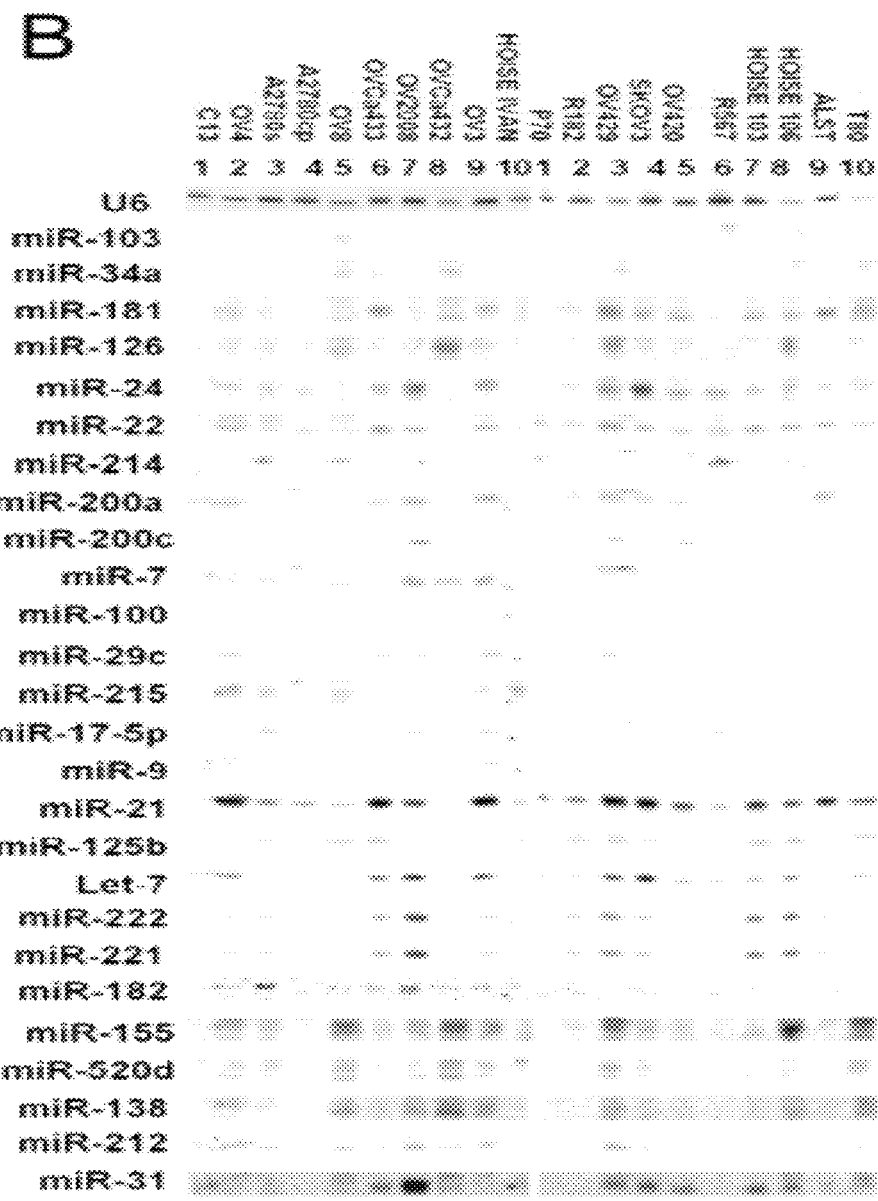
FIG. 19: A series of images of Northern blot analysis of microRNAs in ovarian tumors and ovarian cancer cell lines.

MicroRNA microarray (e.g.; hierarchal clustering) analysis revealed distinct microRNA expression patterns between normal ovarian surface epithelia and primary tumors as well as between HIOSE cells and all ovarian cancer cell lines. We have compared the microRNA expression profiles between primary ovarian tumors and cell lines and identified common changed microRNAs in ovarian cancer as shown in Table 4. We also performed Northern Blot analysis and qRT-PCR analysis and confirmed the deregulated miRNAs that were revealed by the miRNA microarray as shown in FIG. 19. Our work indicates that microRNA expression signatures provides better insight into pathways in ovarian cancer development and progression.

TABLE 4

Comparison of the deregulated miRNAs between primary ovarian tumors and ovarian cancer cell lines

| miRNA Name | Cluster | Fold change | Concodant in tumors |
|---|---|---|---|
| hsa-miR-21 | | 4.4 | Yes |
| hsa-let-7a | let-7a-1/let-7f-1/let-7d, let-7a-2/100, let-7a-3/let-7 | 3.3 | Yes |
| hsa-miR-100 | let-7a-2/100 | 3.3 | Yes |
| hsa-miR-7 | | 3.1 | |
| hsa-miR-221 | 221/222 | 2.8 | Yes |
| hsa-miR-214 | 214/199a-2 | 2.8 | Yes |
| hsa-miR-9 | | 2.8 | Yes |
| hsa-miR-181a | 181a-1/181b-1, 181a-2/181b-2 | 2.8 | Yes |
| hsa-miR-18a | 17/18a/19a/20a/19b-1/92 | 2.7 | |
| hsa-miR-212 | | 2.7 | |
| hsa-let-7c | let-7c/99a | 2.7 | Yes |
| hsa-miR-182 | 182/96/183 | 2.7 | Yes |
| hsa-miR-222 | 221/222 | 2.6 | Yes |
| hsa-miR-200a | 200b/200a/429 | 2.6 | Yes |
| has-miR-30d | 30a, 30b/d, 30c-1/30e, 30c-2 | 2.6 | Yes |
| hsa-miR-29c | 29a/29b-1, 29b-2/29c | 2.6 | Yes |
| hsa-miR-17 | 17/18a/19a/20a/19b-1/92 | 2.4 | |
| hsa-miR-181b | 181a-1/181b-1, 181a-2/181b-2 | 2.2 | Yes |
| hsa-miR-93 | 25/93/106b | −2.1 | |
| hsa-miR-34c | 34b/c | −2.3 | |
| hsa-miR-215 | 215/194-1 | −2.6 | Yes |
| hsa-miR-126 | | −2.7 | Yes |
| hsa-miR-24 | 23a/27a/24-2, 23b/27b/24-1 | −2.8 | Yes |
| hsa-miR-27b | 23b/27b/24-1 | −3.0 | |
| hsa-miR-31 | | −3.6 | |
| hsa-miR-22 | | −3.7 | Yes |
| hsa-miR-125b | | −3.8 | |
| hsa-miR-155 | | −8.9 | Yes |

In several human malignancies, progression from precursor forms to invasive tumor occurs but a similar sequence for ovarian cancer is currently unclear. It was suggested that benign serous and mucinous tumors may progress to low-grade serous and mucinous cancers respectively (e.g. cystadenoma—low malignant potential tumors (LMP)—carcinoma) and that high-grade serous ovarian cancer is likely to arise de novo from genetically altered ovarian surface epithelial cells.

Ovarian cystadenomas are new growths (neoplasms) that develop from the ovarian tissue. They are classified according to the type of fluid they contain—serous or mucinous. Serous cystadenomas are filled with a thin watery fluid while mucinous cystadenomas are filled with a sticky thick gelatinous material. Cystadenomas are normally benign but can become malignant. Low malignant potential tumors account for approximately 15% of all epithelial ovarian cancers. (DiSaia, P. J. et. al., The adnexal mass and early ovarian cancer. In: DiSaia P. J., Creasman, editors. Clinical gynecologic oncology, 6$^{th}$ ed. St. Louis: Mosby-Year Book; 2002. P. 224-56) They are neoplasms that have histologic and biologic features that are intermediate to those of clearly benign and clearly malignant ovarian tumors. Patients with ovarian LMP tumors have a 10 year survival rate of 95%. (Trimble, C. L. et. al., Long term survival and patterns of care in women with ovarian tumors of low malignant potential, Gynecol Oncol, 2002; 86:34-7; Rao, G. G. et. al., Fertility-sparing surgery for ovarian low malignant potential tumors, Gynecol Oncol, 2005; 98:263-66) Ovarian carcinomas are malignant tumors. There are four histological types of ovarian carcinomas: serous, mucinous, endometrioid, and clear cell.

Figure 20:
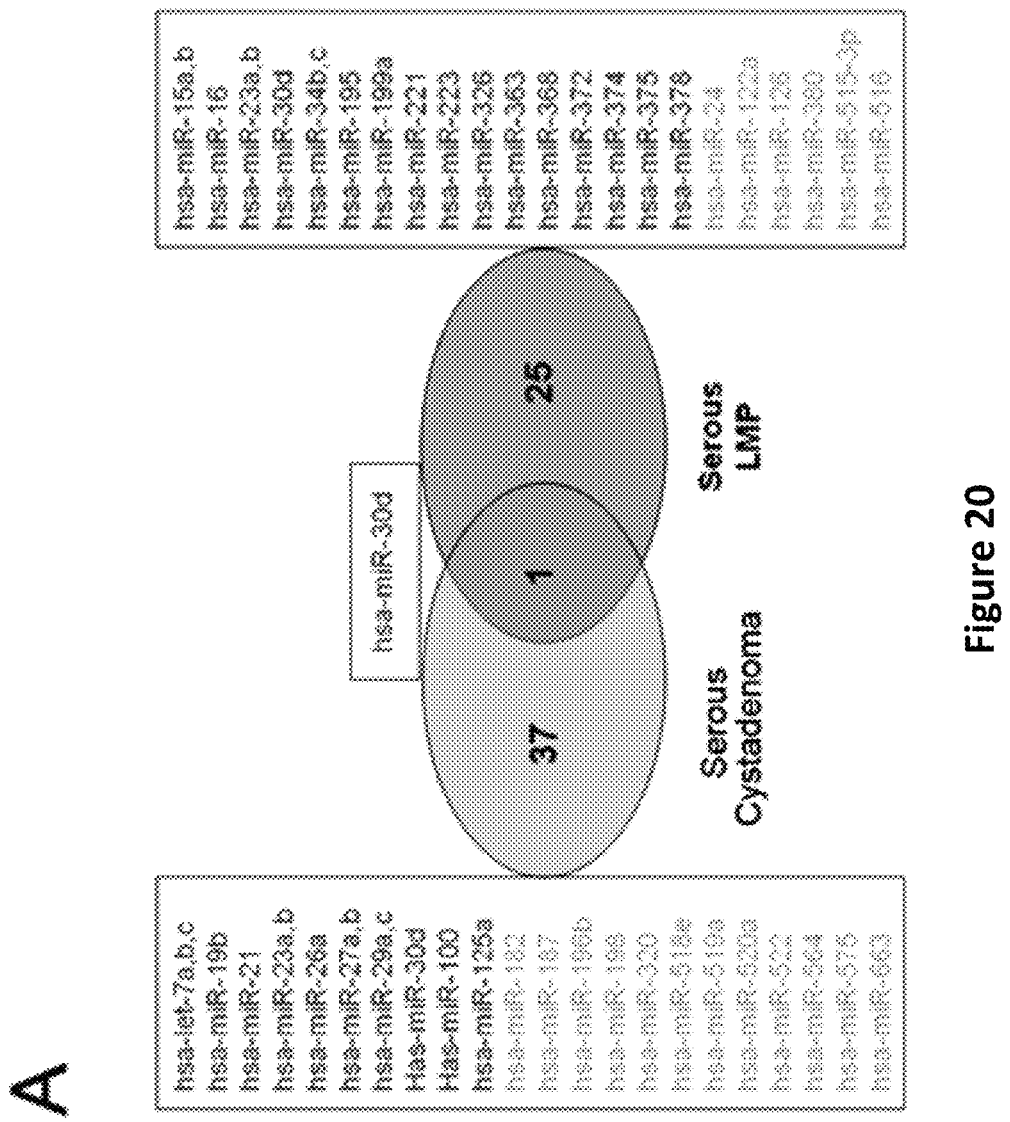
FIG. 20: A series of images of the microRNA expression signatures in serous and mucinous cancers.
Figure 20:
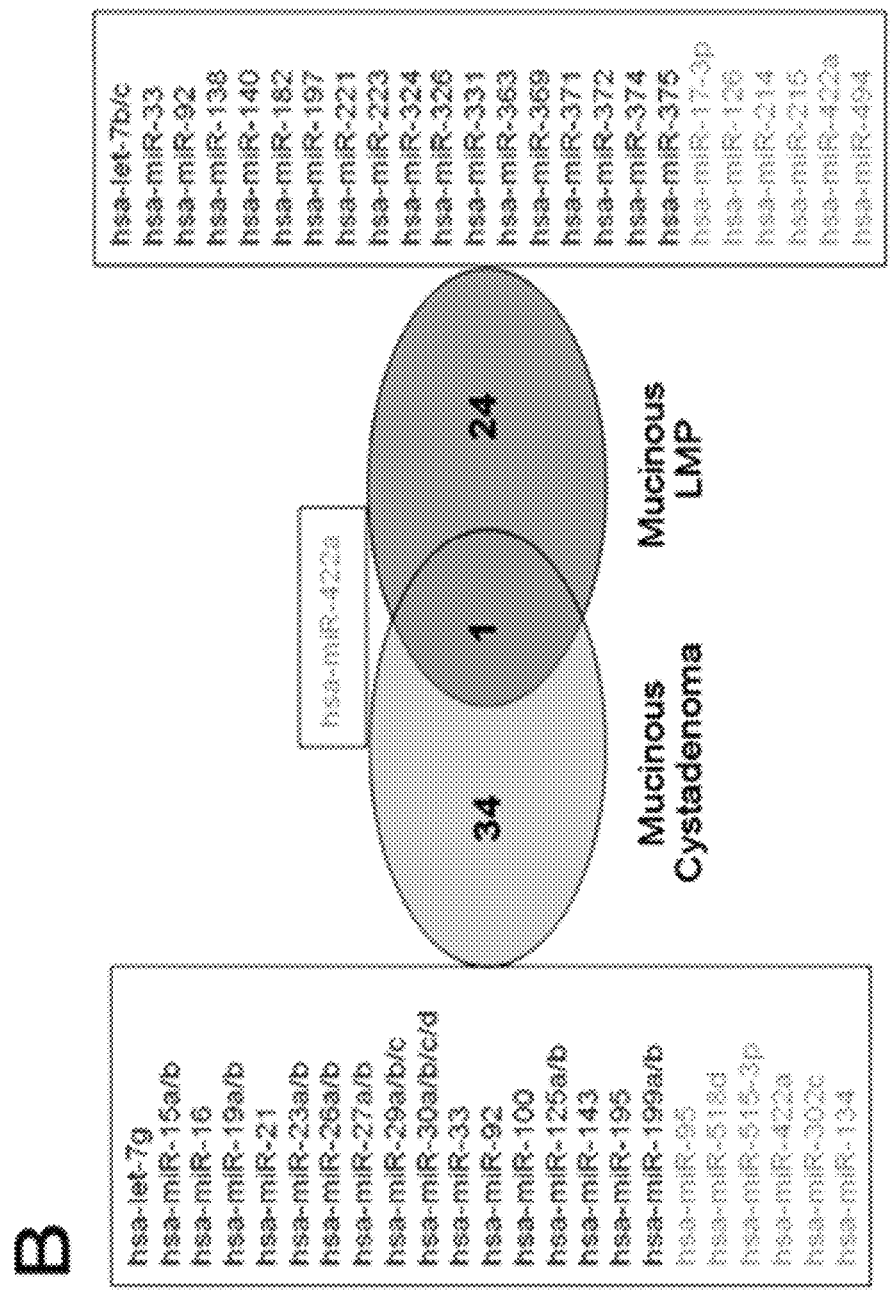
Figure 20:
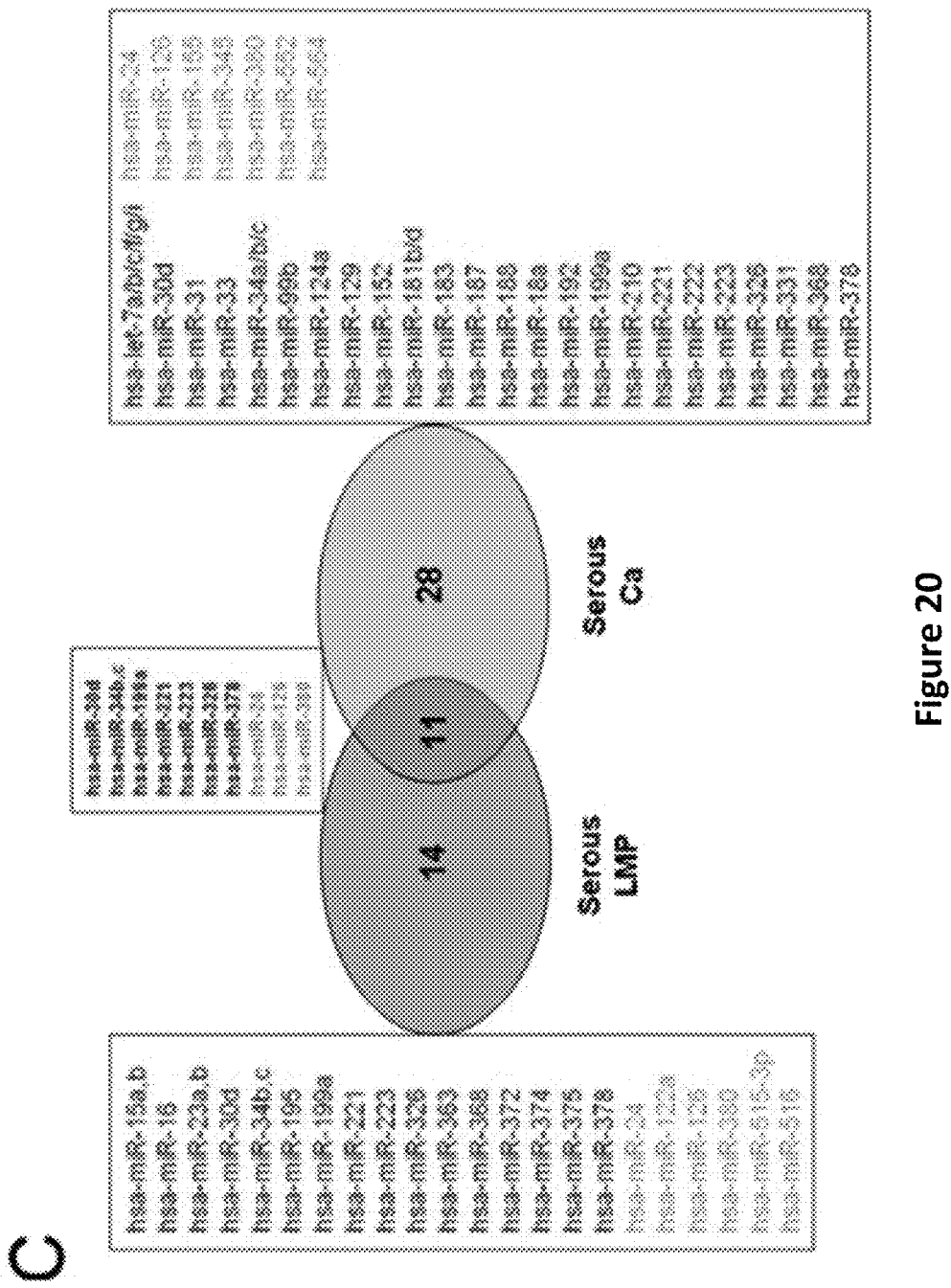
Figure 20:
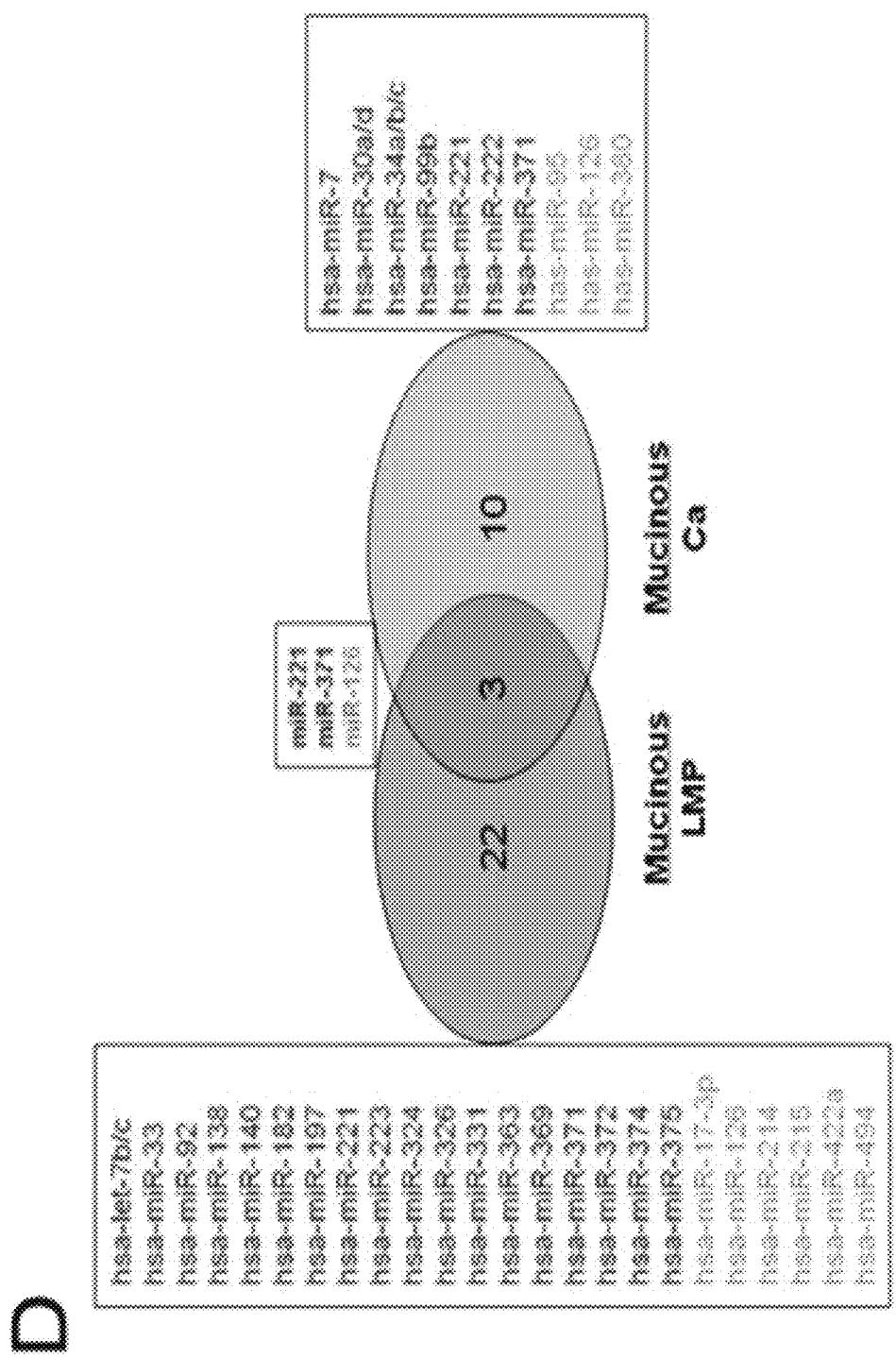

We have found that only a few microRNAs are co-regulated between cystadenoma and LMP as well as between LMP and carcinoma, as shown in FIG. 20. However, the data indicates more microRNAs are co-regulated between serous LMP versus carcinoma as shown in FIG. 20C. We have also found that miR-30d is elevated in cystadenoma, LMP and carcinoma except mucinous LMP and endometrial tumor as shown in FIG. 20. This data indicates that miR-30d may be an early change and may serve as an early diagnostic marker in ovarian cancer. The data also indicates that miRNAs can be important for the development of ovarian cancer but may not be important for the progression of the disease.

Figure 21:
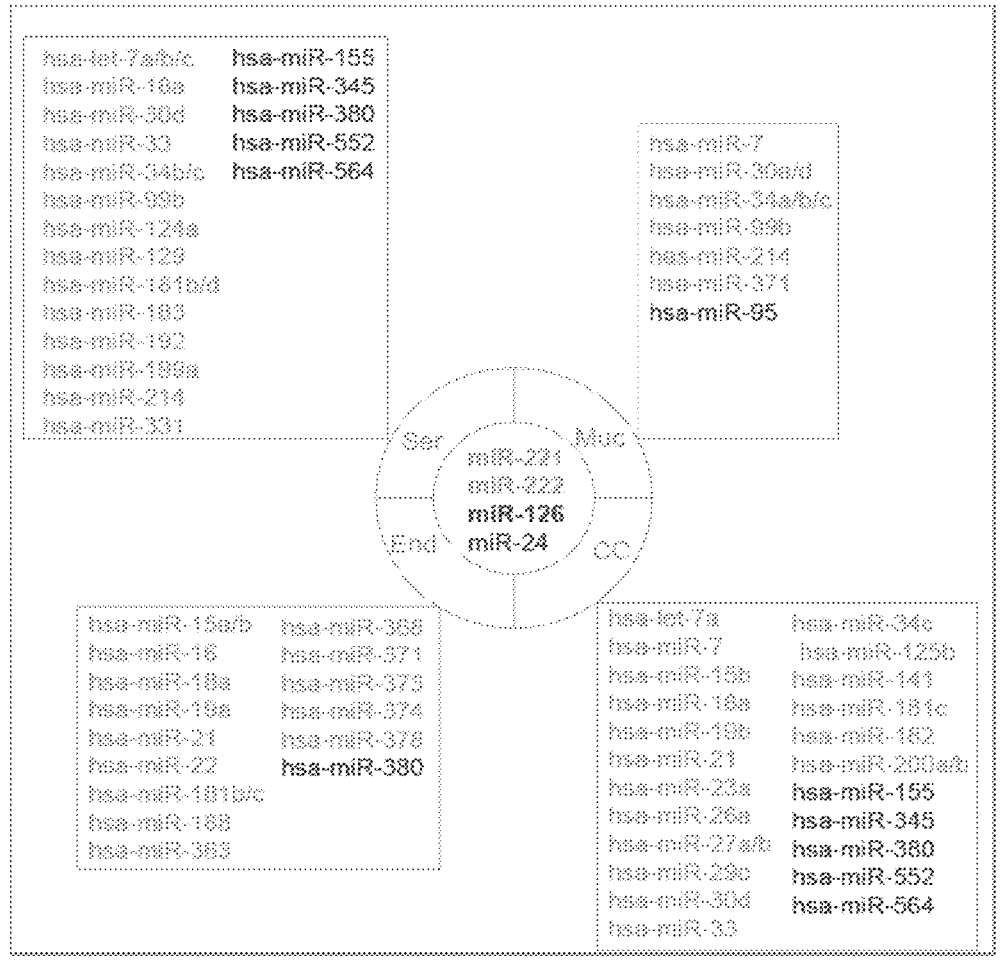
FIG. 21: An image of the microRNA expression profiles in different histological types of cancer. The abbreviations are: Ser or S=serous; End or E endometrioid; Muc or M=mucinous; CC or C=clear cell.

Our research also shows that different histological types of ovarian cancer exhibited distinct micro-RNA expression patterns as shown in FIG. 21. These distinct patterns indicate that microRNAs can be used as markers for differential diagnosis. Our research also shows that a total of four microRNAs are deregulated in all of ovarian carcinoma (serous, mucinous, endometrioid, clear cell). Two of these, miR-221 and miR-222, are upregulated. The upregulated miRNAs can be considered oncogenes that usually promote tumor development by negatively inhibiting tumor suppressor genes and/or genes that control cell differentiation and apoptosis. (Zhang 2007) The other two, miR-126 and miR-24 are downregulated. MicroRNAs that are downregulated can be considered tumor suppressor genes that prevent tumor development by negatively inhibiting oncogenes and/or genes that control cell differentiation or apoptosis. (Zhang 2007) These four microRNAs can be used as biomarkers for diagnosis and prognosis as well as treatment response since microRNA is approximately 22nt RNA, relatively stable, and can be detected in a patient's serum.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

While there has been described an illustrated specific embodiments of a method of diagnosing ovarian cancers through the use of miRNAs, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

What is claimed is:

1. A method of detecting miR-214 in a human ovarian tissue sample, wherein the method consists essentially of measuring an expression level of the miR-214 in the human ovarian tissue sample wherein no other miRNA is measured in the human ovarian tissue sample.

* * * * *